United States Patent [19]

Kukolja

[11] 4,052,387

[45] Oct. 4, 1977

[54] METHOD OF PREPARATION OF 3-METHYLENECEPHAMS

[75] Inventor: Stjepan Kukolja, Carmel, Ind.

[73] Assignee: Eli Lilly and Company, Indianapolis, Ind.

[21] Appl. No.: 673,036

[22] Filed: Apr. 2, 1976

Related U.S. Application Data

[63] Continuation-in-part of Ser. No. 632,733, Nov. 19, 1975, abandoned, which is a continuation-in-part of Ser. No. 536,280, Dec. 24, 1974, abandoned.

[51] Int. Cl.$^2$ .......................................... C07D 501/02
[52] U.S. Cl. ..................................... 544/22; 424/246; 260/239 A; 544/16

[58] Field of Search ..................................... 260/243 C

[56] References Cited

U.S. PATENT DOCUMENTS 3,960,851    6/1976    Kukolja et al. .................. 260/243 C

*Primary Examiner*—Nicholas S. Rizzo
*Attorney, Agent, or Firm*—Steven R. Lammert; Everet F. Smith

[57] ABSTRACT

Penicillin sulfoxide derived azetidinone sulfinyl chlorides and related sulfinic acid derivatives are cyclized to 3-methylenecephams by reaction with Friedel-Crafts catalysts or metathetic cation forming agents.

35 Claims, No Drawings

METHOD OF PREPARATION OF 3-METHYLENECEPHAMS

CROSS-REFERENCE TO RELATED APPLICATION

This application is a continuation-in-part of U.S. application Ser. No. 632,733 filed Nov. 19, 1975, now abandoned, which application was a continuation-in-part of U.S. application Ser. No. 536,280 filed Dec. 24, 1974, now abandoned.

BACKGROUND OF THE INVENTION

Penicillins and more recently cephalosporins have been recognized for their high degree of antibacterial activity and have been used extensively for the treatment of infectious disease in man. There has been a considerable research effort directed toward the chemical modification of these compounds in search of yet more active beta-lactam antibiotics. Much emphasis has been placed specifically on the variation of the $C_6$-acylamino substituent on the penicillin compounds and both the $C_7$-acylamino substituent and the $C_3$-substituent on the cephem compounds.

Recently R. R. Chauvette and P. A. Pennington reported the use of 3-methylenecephams both in the preparation of 7-amino desacetoxycephalosporanic acid and biologically active derivatives thereof [*Journal of Organic Chemistry*, 38, 2994 (1973)], and in the preparation of novel 3-methoxy and 3-halo cephems [*Journal of the American Chemical Society*, 96, 4986 (1974)]. In each case the 3-methylenecepham intermediates were prepared from cephalosporanic acids by first treating the cephalosporanic acids with selected sulfur nucleophiles such as thiourea, thiobenzoic acid, potassium ethyl xanthate or sodium thiosulfate and then reducing the respective product $C_3$-(substituted)thiomethyl cephem derivatives with either Raney nickel in aqueous ethanol or zinc in formic acid-dimethylformamide. The demonstrated versatility of the 3-methylenecephams as intermediates to novel cephem antibiotics has prompted a search for alternative procedures for preparing such compounds from readily available, economic starting materials.

This invention relates to certain azetidinone sulfinic acid derivatives and to a process for preparing 3-methylenecepham sulfoxides from such compounds. More particularly this invention relates to the intramolecular cyclization of penicillin sulfoxide derived monocyclic azetidinone-2-sulfinyl chlorides and sulfinic acid, sulfinate ester, thiosulfinate ester, sulfinamide, and sulfinimide derivatives thereof with Friedel-Crafts catalysts or metathetic cation forming agents.

SUMMARY OF THE INVENTION

This invention is directed to monocyclic azetidinone compounds of the formula

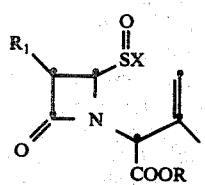

wherein X is a group of the formula $-OR_4$, $-SR_5$ or

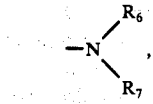

and to a process for preparing 3-methylenecepham sulfoxides, versatile intermediates for the preparation of antibiotic compounds, by cyclization of such azetidinone sulfinic acid derivatives and the corresponding sulfinyl chlorides and sulfinyl bromides by treatment of such compounds with Friedel-Crafts catalysts or metathetic cation-forming agents.

DETAILED DESCRIPTION OF THE INVENTION

In the process of the present invention 3-methylenecepham sulfoxides of the formula

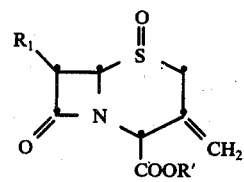

are prepared by reacting a compound of the formula

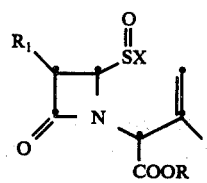

with a Lewis acid type Friedel-Crafts catalyst, a Bronsted proton acid type Friedel-Crafts catalysts or a metathetic cation-forming agent in a dry inert organic solvent, or dissolving such compound in a Bronsted acid selected from the group consisting of methanesulfonic acid, trifluoromethanesulfonic acid, trifluoroacetic acid, trichloroacetic acid and dichloroacetic acid; wherein in the above formulae R is a carboxylic acid protecting group;
R' is R or hydrogen;
$R_1$ is (1) an imido group of the formula

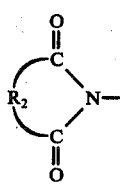

wherein $R_2$ is $C_2$-$C_4$ alkenylene, $C_2$-$C_4$ alkylene, 1,2-phenylene, 1,2-cyclohexenylene; or
2. an amido group of the formula

wherein $R_3$ is
a. hydrogen, $C_1$-$C_3$ alkyl, halomethyl, cyanomethyl or 3-(2'-chlorophenyl)-5-methylisoxazol-4-yl;

b. benzyloxy, 4-nitrobenzyloxy, 2,2,2-trichloroethoxy, tert-butoxy, or 4-methoxybenzyloxy;
c. the group R" wherein R" is phenyl or phenyl substituted with 1 or 2 substituents independently selected from the group consisting of halo, protected hydroxy, nitro, cyano, trifluoromethyl, $C_1-C_3$ alkyl, and $C_1-C_4$ alkoxy;
d. an arylalkyl group of the formula

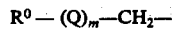

wherein $R^0$ is R" as defined above, 2-thienyl, 3-thienyl, or 1,4-cyclohexyldienyl, $m$ is 0 or 1, and Q is 0 or S subject to the limitation that when $m$ is 1, $R^0$ is R";
e. a substituted arylalkyl group of the formula

wherein $R^0$ is defined above and W is protected hydroxy, or protected amino;
3. an imido group of the formula

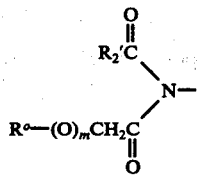

wherein $R^0$ and $m$ are as defined hereinabove and $R_2'$ is $C_1-C_3$ alkyl, $C_1-C_6$ haloalkyl, $C_1-C_3$ alkoxy or trichloroethoxy; or $R_1$ is
4. an imidazolidinyl group of the formula

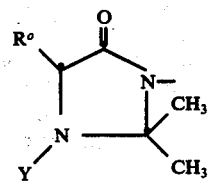

wherein $R^0$ is as defined above and Y is acetyl or nitroso; and X is
1. chloro or bromo;
2. a group of the formula —$OR_4$ wherein $R_4$ is hydrogen, $C_1-C_{10}$ alkyl, aryl ($C_1-C_3$ alkyl) or $C_1-C_6$ haloalkyl;
3. a group of the formula —$SR_5$ wherein $R_5$ is $C_1-C_6$ alkyl, aryl or aryl ($C_1-C_3$ alkyl); or
4. a group of the formula

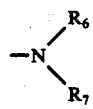

wherein
a. $R_6$ is hydrogen and $R_7$ is hydrogen, R" as defined hereinabove, or a group of the formula —$NHR_8$ wherein $R_8$ is aminocarbonyl, $C_1-C_3$ alkylaminocarbonyl, $C_1-C_3$ alkoxycarbonyl, $C_1-C_3$ alkylcarbonyl or tosyl; or wherein b. $R_6$ is —$COOR_9$ or —$COR_9$ and $R_7$ is —NH-$COOR_9$ or —$NHCOR_9$ wherein $R_9$ is $C_1-C_6$ alkyl, or phenyl; or wherein
c. $R_6$, $R_7$ and the nitrogen atom to which they are bonded taken together form an imido group of the formula

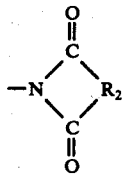

wherein $R_2$ is as defined hereinabove:
and when $R_6$ is —$COOR_9$ or —$COR_9$ and $R_7$ is —NH-$COOR_9$ or —$NHCOR_9$, $R_3$ is additionally a heteroarylmethyl group of the formula R""$CH_2$—
wherein R"" is 2-furyl, 3-furyl, 2-thiazolyl or 5-isoxazolyl;
with the limitations that when X is bromo, $R_1$ is only an imido group of the formula

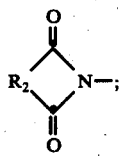

when the cyclizing agent is a metathetic cation-forming agent or a Lewis acid, X is only chloro or bromo; and when R is an acid labile carboxylic acid protecting group, the product is a 3-methylenecepham-4-carboxylic acid sulfoxide.

This invention is also directed to compounds of the formula

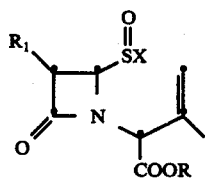

wherein $R_1$, R and X are as defined hereinabove with the exception that X is other than chloro, bromo, or a group of the formula

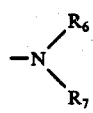

wherein $R_6$ is —$COOR_9$ or —$COR_9$ and $R_7$ is —NH-$COOR_9$ or —$NHCOR_9$.

In the foregoing definition of the process of the present invention the term "$C_1-C_3$ alkyl" refers to methyl, ethyl, n-propyl, or isopropyl. The term "$C_1-C_{10}$ alkyl" includes methyl, ethyl, propyl, isopropyl, cyclohexyl, sec-butyl, heptyl, octyl, isooctyl, decyl, menthyl and like alkyl groups. "$C_1-C_6$ Haloalkyl" represents groups such as chloromethyl, bromoethyl, iodoethyl, 2-chloropropyl, 2-chlorocyclohexyl, 2-chlorobutyl and like groups. The term "aryl($C_1-C_3$alkyl)" includes benzyl, 2-phenylethyl, 2-phenyl propyl, 4-chlorobenzyl, naphthylmethyl, 3-(2-nitrophenyl) propyl and like groups. Exemplary of the term $C_1$-$C_3$ alkoxycarbonyl are methoxycarbonyl, ethoxycarbonyl, and isopropoxycarbonyl. Exemplary of "halomethyl" groups are chloromethyl, bromomethyl or iodomethyl. Imido groups represented when $R_2$ is $C_2$-$C_4$ alkenylene are maleimido, 3-ethylmaleimido, 3,4-dimethylmaleimido, and like imido groups. Imido groups represented when R is 1,2-cyclohexenylene or 1,2-phenylene are 3,4,5,6-tetrahydrophthalimido or phthalimido respectively.

When in the above definition R" represents a substituted phenyl group, R" can be a mono or disubstituted halophenyl group such as 4-chlorophenyl, 2,6-dichlorophenyl, 2,5-dichlorophenyl, 3,4-dichlorophenyl, 3-chlorophenyl, 3-bromophenyl, 4-bromophenyl, 3,4-dibromophenyl, 3-chloro-4-fluorophenyl, 2-fluorophenyl and the like; a protected hydroxy phenyl group such as 4-benzyloxyphenyl, 3-benzyloxyphenyl, 4-tert-butoxyphenyl, 4-tetrahydropyranyloxyphenyl, 4-(4-nitrobenzyloxy)phenyl, 2-phenacyloxyphenyl, 4-benzhydroxyphenyl, 4-trityloxyphenyl and like groups; a nitrophenyl group such as 3-nitrophenyl or 4-nitrophenyl; a cyanophenyl group, for example, 4-cyanophenyl; a mono or dialkyl substituted phenyl group such as 4-methylphenyl, 2,4-dimethylphenyl, 2-ethylphenyl, 4-isopropylphenyl, 4-ethylphenyl, 3-n-propylphenyl and the like; a mono or dialkoxyphenyl group, for example, 2,6-dimethoxyphenyl, 4-methoxyphenyl, 3-ethoxyphenyl, 4-isopropoxyphenyl, 4-tert-butoxyphenyl, 3-ethoxy-4-methoxyphenyl and the like. Also, R" represents disubstituted phenyl groups wherein the substituents can be different for example, 3-methyl-4-methoxyphenyl, 3-chloro-4-benzyloxyphenyl, 2-methoxy-4-bromophenyl, 4-ethyl-2-methoxyphenyl, 3-chloro-4-nitrophenyl, 2-methyl-4-chlorophenyl and like disubstituted phenyl groups bearing different substituents.

The term "protected amino" as employed in the above definition has reference to an amino group substituted with one of the commonly employed amino blocking groups such as the tert-butoxycarbonyl group (t-BOC); the benzyloxycarbonyl group, the 4-methoxybenzyloxycarbonyl group, the 4-nitrobenzyloxycarbonyl group, the 2,2,2-trichloroethoxycarbonyl group, or the 1-carbomethoxy-2propenyl group formed with methyl acetoacetate. Like amino protecting groups such as those described by J. W. Barton in "Protective Groups in Organic Chemistry," J. F. W. McOmie, Ed., Plenum Press, New York, N.Y., 1973, Chapter 2 shall be recognized as suitable.

The term "protected hydroxy" has reference to the readily cleavable groups formed with an hydroxyl group such as the formyloxy group, the chloroacetoxy group, the benzyloxy group, the benzhydryloxy group, the trityloxy group, the 4-nitrobenzyloxy group, the trimethylsilyloxy group, the phenacyloxy group, the tert-butoxy group, the methoxymethoxy group, the tetrahydropyranyloxy group, and the like. Other hydroxy protecting groups, including those described by C. B. Reese in "Protective Groups in Organic Chemistry", supra, Chapter 3 shall be considered as within the term "protected hydroxy" as used herein.

The term "carboxylic acid protecting group" has reference to the commonly used carboxylic acid protecting groups employed to block or protect the carboxylic acid functionality while reactions involving other functional sites of the compound are carried out. Such carboxy protecting groups are noted for their ease of cleavage by hydrolytic or by hydrogenolytic methods to the corresponding carboxylic acid. Examples of carboxylic acid ester protecting groups include methyl, tert-butyl, benzyl, 4methoxybenzyl, $C_2$-$C_6$ alkanoyloxymethyl, 2-iodoethyl, 4-nitrobenzyl, diphenylmethyl (benzhydryl), phenacyl, 4-halophenacyl, dimethylallyl, 2,2,2-trichloroethyl, tri($C_1$-$C_3$alkyl)silyl, succinimidomethyl and like ester forming moieties. Other known carboxy protecting groups such as those described by E. Haslam in "Protective Groups in Organic Chemistry", supra, Chapter 5, shall be recognized as suitable. The nature of such ester forming groups is not critical.

When the azetidinone sulfinic acid derivative starting material for the process of this invention is protected with an acid labile carboxy protecting group such as 4-methoxybenzyl, benzhydryl, tert-butyl or tri($C_1$-$C_3$alkyl)silyl the product of the cyclization of the present invention is an 3-exomethylenecepham sulfoxide acid. Likewise, if the starting materials have similar acid labile hydroxy or amino protecting groups, such groups will usually be removed under the acidic conditions of the present cyclization process. The removal of certain acid labile protecting groups under the reaction conditions of the present process is not a critical feature of the present invention. The protecting groups on the azetidinone starting materials for the process of this invention are there present because of the necessity of protecting their precursor penicillin sulfoxides during the preparation of the intermediate azetidinone sulfinyl halides. Thus, the primary purpose of the protecting groups is to protect the reactive functional groups during the preparation of the starting materials. The nature of the protecting group is not critical to the present process. No significant reduction in yield of exomethylenecepham sulfoxide is noted when acid labile protecting groups are employed. In such case, the only difference is that the products are typically cepham acids instead of cepham esters. Since subsequent conversions are usually contemplated for the exomethylenecepham sulfoxide products of the present invention, it is preferred that the reactive functional groups on these products remain protected during the cyclization process of this invention. Non-acid labile protecting groups are therefore preferred. The preferred carboxylic acid ester protecting groups are methyl, 2-iodoethyl, 4-nitrobenzyl, 4-halophenacyl and 2,2,2-trichloroethyl.

In the foregoing definitions, hydroxy, amino, and carboxy protecting groups are not exhaustively defined. The function of such groups is to protect the reactive functional groups during the preparation of the starting materials and then be removed at some later point in time without disrupting the remainder of the molecule. Many such protective groups are well known in the art and the use of other groups equally applicable to the process and compounds of the present invention shall be recognized as suitable. Thus, there is no novelty or inventiveness asserted with regard to the "protecting groups" alluded to in this specification.

Representative of the acylamino group,

as defined hereinabove are formamido, acetamido, propionamide, butyramido, 2-pentenoylamino, cyanoacetamido, chloroacetamido, bromoacetamido, 5-tert-butoxycarbonylamino-5-tert-butoxycarbonylvaleramido, and the like.

Illustrative of the particular acylamino group,

are benzamido, 2,6-dimethoxybenzamido, 4-chlorobenzamido, 4-methylbenzamido, 3,4-dichlorobenzamido, 4-cyanobenzamido, 3-bromobenzamido, 3-nitrobenzamido and the like.

Exemplary of the acylamino group

when $R_3$ is a group of the formula $R^o(Q)_mCH_2$— and $m$ is 0, are cyclohexa-1,4-dienylacetamido, phenylacetamido, 4-chlorophenylacetamido, 3-methoxyphenylacetamido, 3-cyanophenylacetamido, 3-methylphenylacetamido, 4-bromophenylacetamido, 4-ethoxyphenylacetamido, 4-nitrophenylacetamido, 3,4-dimethoxyphenylacetamido 2-thienylacetamido, 3-thienylacetamido and the like; and when $m$ is 1 and Q is 0, representative acylamino groups are phenoxyacetamido, 4-cyanophenoxyacetamido, 4-chlorophenoxyacetamido, 3,4-dichlorophenoxyacetamido, 2-chlorophenoxyacetamido, 4-methoxyphenoxyacetamido, 2-ethoxyphenoxyacetamido, 3,4-dimethylphenoxyacetamido, 4-isopropylphenoxyacetamido, 3-cyanophenoxyacetamido, 3-nitrophenoxyacetamido and like substituted phenoxyacetamido groups; and when $m$ is 1 and Q is S, representative groups are phenylthioacetamido, 2,5-dichlorophenylthioacetamido, 4-bromophenylthioacetamido, 4-methoxyphenylthioacetamido, 4-tolylthioacetamido and like substituted phenylthioacetamido groups.

Illustrative of the acylamino groups when $R_3$ is a substituted arylalkyl group of the formula $$R^o-\underset{W}{\underset{|}{CH}}-$$

and when W is protected hydroxy are 2-formyloxy-2-phenylacetamido, 2-benzyloxy-2-(4-methoxyphenyl)acetamido, 2-(4-nitrobenzyloxy)-2-(3-chlorophenyl)acetamido, 2-chloroacetoxy-2-(4-methoxyphenyl)acetamido, 2-benzyloxy-2-phenylacetamido, 2-trimethylsilyloxy-2-(4-chlorophenyl)acetamido, 2-benzhydryloxy-2-phenylacetamido and like groups. Representative of such groups when W is protected amino are 2-(4-nitrobenzyloxycarbonylamino)-2-phenylacetamido, 2-(2,2,2-trichloroethoxycarbonylamino)-2-phenylacetamido, 2-chloroacetamido-2-(1,4-cyclohexadien-1-yl)acetamido, 2-(4-methoxybenzyloxycarbonylamino)-2-(4-methoxyphenyl)acetamido, 2-benzhydryloxycarbonylamino-2-phenylacetamido, 2-(1-carbomethoxy-2-propenyl)amino-2-phenylacetamido, 2-(4-nitrobenzyloxycarbonylamino)-2-(2-thienyl)acetamido and like groups.

Representative of $R_1$ wherein $R_1$ is an imido group of the formula

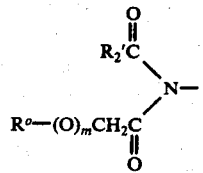

are N-acetyl-N-phenylacetylamino, N-trichloroethoxycarbonyl-N-phenoxyacetylamino, N-propoxycarbonyl-N-(4-chlorophenoxy)acetylamino, N-(2-bromoacetyl)-N-phenoxyacetylamino, and like acyclic imido groups.

Exemplary of the acylamino group

when $R_3$ is a heteroarylmethyl group of the formula $R''''—CH_2$— are 2-furylacetamido, 3-furylacetamido, a 2-thiazolylacetamido group of the formula

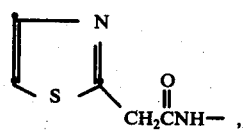

or a 5-isoxazolylacetamido group of the formula

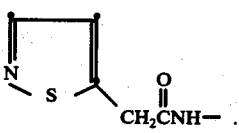

Representative of $R_1$ when $R_1$ is an imidazolidinyl group of the formula

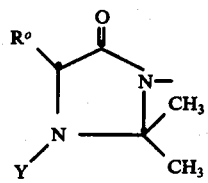

are the 2,2-dimethyl-3-nitroso-5-oxo-4-phenyl-1-imidazolidinyl group, the 2,2-dimethyl-3-nitroso-5-oxo-4-(4-benzyloxyphenyl)-1-imidazolidinyl group, the 2,2-dimethyl-3-acetyl-5-oxo-4-(1,4-cyclohexadien-1-yl)-1-imidazolidinyl group, the 2,2-dimethyl-3-nitroso-5-oxo-4-(2-thienyl)-1-imidazolidinyl group and like substituted imidazolidinyl groups.

In general, the process of this invention is directed to the cyclization of penicillin sulfoxide derived azetidinone sulfinic acid derivatives by the Friedel-Crafts-catalyst induced intramolecular reaction of the sulfinyl and olefinic functionalities on the azetidinone ring. This internal alkylsulfination reaction can be regarded as an analog of a Friedel-Crafts acylation reaction, in which a sulfinyl group

is substituted for a carbonyl group

and the product is a sulfoxide instead of a ketone. The literature contains at least three reports of Friedel-Crafts type sulfinylation reactions. Specifically, the intermolecular arenesulfinylation of aromatics giving diaryl sulfoxides has been described [C. Courtot and J. Frenkiel, *C. R. Acad. Sci.*, 199, 557 (1934); George A. Olah and Jun Nishimura, *J. Org. Chem.*, 39, 1203 (1973); and Irwin B. Douglass and Basil Said Farah, *J. Org. Chem.*, 23, 805 (1958)]. In an analogous reaction alkyl or arylsulfenyl chlorides react with aromatic hydrocarbons in the presence of aluminum chloride catalyst to give thioethers with good yields [H. Britzinger and M. Langheck, *Ber.*, 86, 557 (1953)]. The reaction of alkyl or arylsulfonic acid chlorides with aromatics to provide sulfones has been more extensively investigated. See e.g., George A. Olah, "Friedel-Crafts Chemistry," John Wiley and Sons, Inc., New York, N.Y., 1973, pp. 122–123, 146, 507. There have been no previous reports of intramolecular alkylsulfinylation of the sort described hereinbelow. The intramolecular cyclization of carboxylic acids and derivatives thereof with Friedel-Crafts catalysts to prepare cyclic ketones is, however, well documented in the chemical literature. See William S. Johnson in "Organic Reactions," Roger Adams et al., Eds., John Wiley and Sons, Inc., New York, N.Y., 1944, Chapter 4, pp. 130–177 and "Friedel-Crafts Chemistry", supra. It has been found in this invention that conventional Friedel-Crafts acylation procedures, including reaction conditions, solvents, and catalysts reagents are successfully applied generally to the intramolecular cyclization of the azetidinone sulfinyl chlorides and derivatives thereof of this invention.

The azetidinone sulfinyl chloride starting materials for the process and compounds of the present invention are derived from the corresponding known penicillin sulfoxide esters by reacting such esters at elevated temperatures with a reagent serving as a source of positive halogen, preferably an N-haloimide such as N-chlorosuccinimide. The conversion of 6-imido penicillin sulfoxide esters to the corresponding sulfinyl chlorides with sulfuryl chloride has been described in the literature [S. Kukolja and S. R. Lammert, *Angew. Chem.*, 12, 67–68 (1973)]. Generally the sulfinyl chloride starting materials for the process of this invention are prepared by reacting a penicillin sulfoxide ester with about 1.1 equivalents of N-chlorosuccinimide in a dry inert organic solvent, preferably 1,1,2-trichloroethane or toluene at a temperature of about 70° to 120° C., the preferred temperature being dependent primarily on the nature of the $C_6$-substituent. The conversion of $C_6$-imido penicillin sulfoxides is usually accomplished at 70°–100° C., while slightly higher temperatures (100°–120° C.) are preferred for the sulfinyl chloride preparation from $C_6$-acylamino penicillin sulfoxides. The reaction is usually complete in 45–90 minutes at the preferred reaction temperature. The penicillin sulfoxide ester precursors to the sulfinyl chlorides are either known or readily available compounds, many of which have been used in the preparation of cephem compounds. They are prepared from known 7-acylamino and 7-imido penicillin acids by (1) esterification and (2) subsequent oxidation, usually with metachloroperbenzoic acid or sodium periodate.

Exemplary of the preparation of the azetidinone sulfinyl chloride starting materials for the compounds of the present invention is the following brief description of the preparation of 4'-nitrobenzyl 3-methyl-2-(2-chlorosulfinyl-4-oxo-3-acetamido-1-azetidinyl)-3-butenoate: A solution of 5 mmoles of 4'-nitrobenzyl 6-acetamidopenicillanate 1-oxide in 200 ml. of toluene is heated to reflux and dried azeotropically by allowing approximately 20 ml. of toluene to be distilled from the mixture. After cooling the mixture briefly, 5.5 mmoles of N-chlorosuccinimide is added. The mixture is refluxed for 90 minutes after which time the solution is cooled to room temperature and filtered. Evaporation in vacuo of the filtrate provides 4'-nitrobenzyl 3-methyl-2-(2-chlorosulfinyl-4-oxo-3-acetamido-1-azetidinyl)-3-butenoate as a froth. The product azetidinone sulfinyl chlorides thus obtained can be employed in the cyclization process of this invention directly without purification. Indeed, it is often the case where the Friedel-Crafts catalyst reagent is added directly to the final reaction mixture of the preparation of the azetidinone sulfinyl chloride.

In a reaction analogous to the reaction of penicillin sulfoxide esters with NCS to provide azetidinone sulfinyl chlorides, penicillin sulfoxide esters having an imido group at C-6 can be reacted with N-bromosuccinimide (NBS) to provide the corresponding azetidinone sulfinyl bromides. The reaction conditions for this conversion are identical to those employed in the aforedescribed sulfinyl chloride preparation using NCS. The aforedescribed azetidinone sulfinyl chlorides and the corresponding sulfinyl bromides exhibit similar chemical reactivity in regard to the cyclizing agents described in detail hereinbelow.

The azetidinone sulfinic acids, compounds of this invention of the formula

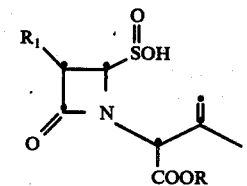

wherein R and $R_1$ are as defined hereinabove, are generally prepared from the corresponding sulfinyl chlorides by slurrying an ethyl acetate solution of the sulfinyl chloride with an aqueous sodium bicarbonate solution at room temperature for about one hour. The aqueous layer containing the sulfinic acid salt is separated, washed with ethyl acetate, layered with another portion of ethyl acetate and then acidified. The organic layer is separated, washed with brine, dried over anhydrous sodium sulfate, and then evaporated in vacuo to dryness. The sulfinic acids thereby isolated are generally obtained as colorless amorphous solids.

Representative of the sulfinic acids of this invention are the following:

4'-nitrobenzyl 3-methyl-2-(2-sulfino-4-oxo-3-phenylacetamido-1-azetidinyl)-3-butenoate, 2',2',2'-trichloroethyl 3-methyl-2-(2-sulfino-4-oxo-3-acetamido-1-azetidinyl)-3-butenoate, 2'-iodoethyl 3-methyl-2-(2-sulfino-4-oxo-3-chloroacetamido-1-azetidinyl)-3-butenoate, 4'-methoxybenzyl 3-methyl-2-(2-sulfino-4-oxo-3-phthalimido-1-azetidinyl)-3-butenoate, tert-butyl 3-methyl-2-[2-sulfino-4-oxo-3-(2-bromoacetamido)-1-azetidinyl]-3-butenoate, benzhydryl 3-methyl-2-[2-sulfino-4-oxo-3-(4-chlorophenoxyacetamido)-1-azetidinyl]-3-butenoate, 4'-nitrobenzyl 3-methyl-2-[2-sulfino-4-oxo-3-(4-nitrobenzyloxycarbonylamino)-1-azetidinyl]-3-butenoate, 2',2',2'-trichloroethyl 3-methyl-2-[2-sulfino-4-oxo-3-(2,2-dimethyl-3-nitroso-5-oxo-4-phenyl-1-imidazolidinyl)-1-azetidinyl]-3-butenoate, 2'-iodoethyl 3-methyl-2-[2-sulfino-4-oxo-3-(2-thienylacetamido)-1-azetidinyl]-3-butenoate, and 4-nitrobenzyl 3-methyl-2-[2-sulfino-4-oxo-3-(4-chlorobenzamido)-1-azetidinyl]-3-butenoate.

It shall be recognized that other derivatives of the azetidinone sulfinyl chlorides, including sulfinate esters, thiosulfinate esters, mixed carboxylic and sulfonic anhydrides, and sulfinamide and sulfinimide derivatives thereof, can be prepared from the sulfinic acids of this invention and from their precursor sulfinyl chlorides. Such derivatives can be prepared by well-known conventional procedures employed in the preparation of carboxylic acid derivatives e.g. esters, thioesters, anhydrides, amides and imides from carboxylic acids and carboxylic acid chlorides. Some azetidinone sulfinamide derivatives have been prepared directly from penicillin sulfoxides [S. Terao, T. Matsuo, S. Tsushima, N. Matsumoto, T. Miyawaki, and M. Miyamoto, *J. Chem. Soc (C)*, 1304 (1972)]. It shall further be recognized that such derivatives can be cyclized to 3-methylenecepham sulfoxide compounds by the procedures and conditions set forth hereinbelow.

Azetidinone sulfinic acid esters (sulfinates) of the present invention of the formula

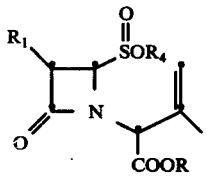

wherein R and $R_1$ are as defined hereinabove and $R_4$ is $C_1-C_{10}$ alkyl, aryl($C_1-C_3$alkyl) or $C_1-C_6$ haloalkyl are prepared from the aforedescribed penicillin sulfoxide derived azetidinone sulfinyl chlorides by reacting the sulfinyl chloride with the corresponding $C_1-C_{10}$alkanol, aryl($C_1-C_3$ alkanol) or $C_1-C_6$ haloalkanol respectively. Typically the sulfinic acid esters are prepared by adding the desired alcohol directly to the reaction mixture in which the azetidinone sulfinyl chloride has been generated from a penicillin sulfoxide. The product sulfinic acid ester is then isolated using standard isolation techniques including evaporation, crystallization and chromatography.

Exemplary of alcohols which can be employed in the preparation of the sulfinic acid esters of this invention are methanol, ethanol, isopropanol, cyclohexanol, 4-chlorocyclohexanol, sec-butanol, n-heptanol, menthol, benzyl alcohol, 2-phenylethanol, 3-phenylpropanol, 2-chlorobenzyl alcohol, 4-methoxybenzyl alocohol, 2-(4-nitrophenyl) ethanol, 2-chloroethanol, 2-bromoethanol, 3-bromocyclohexanol, 4-chlorobutanol, 3-chloropropanol and like alcohols.

Representative of the azetidinone sulfinic acid esters of the present invention are 4'-nitrobenzyl 3-methyl-2-(2-isobutoxysulfinyl-4-oxo-3-acetamido-1-azetidinyl)-3-butenoate, benzhydryl 3-methyl-2-[2-(2-chloropropoxysulfinyl)-4-oxo-3-phenoxyacetamido-1-azetidinyl]-3-butenoate, 2',2',2', -trichloroethyl 3-methyl-2-[2-(2-bromoethoxysulfinyl)-4-oxo-3-(2-formyloxy-2-phenylacetamido)-1-azetidinyl]-3-butenoate, 2'-iodoethyl 3-methyl-2-[2-(4-bromobenzyloxy-sulfinyl)-4-oxo-3-phthalimido-1-azetidinyl]-3-butenoate, tert-butyl 3-methyl-2-(2-methoxysulfinyl-4-oxo-3-benzyloxycarbonylamino-1-azetidinyl)-3-butenoate, 4'-chlorophenacyl 3-methyl-2-[2-(2-phenylisopropoxysulfinyl)-4-oxo-3-(2-thienylacetamido)-1-azetidinyl]-3-butenoate, 4'-methoxybenzyl 3-methyl-2-[2-cyclohexyloxysulfinyl-4-oxo-3-(2,2-dimethyl-3-nitroso-5-oxo-4-phenyl-1-imidazolidinyl-1-azetidinyl]-3-butenoate, and methyl 3-methyl-2-[2-(3-phenylpropoxysulfinyl)-4-oxo-3-(4-chlorophenoxyacetamido)-1-azetidinyl]-3-butenoate.

Azetidinone thiosulfinate esters of the present invention of the formula

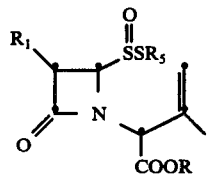

wherein R and $R_1$ are as defined hereinabove and $R_5$ is $C_1-C_6$ alkyl, aryl, or aryl ($C_1-C_3$ alkyl) are prepared from the aforedescribed azetidinone sulfinyl chlorides by their reaction with the corresponding $C_1-C_6$alkylthiol, arylthiol or aryl ($C_1-C_3$alkyl) thiol respectively. The thiosulfinate esters are prepared and isolated using standard experimental techniques. Their preparation is directly analogous to the preparation of carboxylic acid thioesters from carboxylic acid chlorides.

Representative of thiols or mercaptans which can be employed in the preparation of the azetidinone thiosulfinate esters of this invention are methanethiol, ethanethiol, 2-propanethiol, 2-methyl-2-propanethiol, cyclohexanethiol, 2-pentanethiol, 1-butanethiol, thiophenol, 4-chlorothiophenol, 2-phenylethanethiol, and benzylmercaptan.

Representative of the azetidinone thiosulfinate esters of this invention are

4'-nitrobenzyl 3-methyl-2-(2-methylthiosulfinyl 4-oxo-3-formamido-1-azetidinyl)-3-butenoate, 2'-iodoethyl 3-methyl-2-[2-(2-methyl-1-propanethiosulfinyl)-4-oxo-3-(4-methoxybenzyloxycarbonylamino)-1-azetidinyl]-3-butenoate, 2',2', 2'-trichloroethyl 3-methyl-2-[2-(1-hexanethiosulfinyl)-4-oxo-3-(4-trifluoromethylbenzamido)-1-azetidinyl]-3-butenoate, benzhydryl 3-methyl-2-[2-benzylthiosulfinyl-4-oxo-3-(4-methylphenoxyacetamido)-1-azetidinyl]-3-butenoate, and tert-butyl 3-methyl-2-[2-phenylthiosulfinyl-4-oxo-3-(4-nitrobenzyloxycarbonylamino)-1-azetidinyl]-3-butenoate.

Also compounds of the present invention are the sulfinamide and sulfinimide derivatives of the penicillin sulfoxide derived azetidinone sulfinyl chlorides. Such compounds are represented by the formula

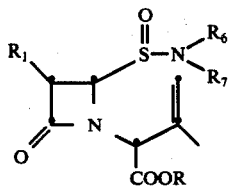

wherein R and $R_1$ are as defined hereinabove and wherein (a) $R_6$ is hydrogen and $R_7$ is hydrogen, R" as defined hereinabove, or a group of the formula —$NHR_8$ wherein $R_8$ is aminocarbonyl, $C_1$–$C_3$ alkylaminocarbonyl, $C_1$–$C_3$ alkoxycarbonyl, $C_1$–$C_3$ alkylcarbonyl or tosyl; or wherein (b) $R_6$ and $R_7$ and the nitrogen atom to which they are bonded taken together form an imido group of the formula

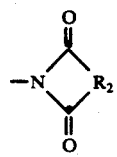

wherein $R_2$ is as defined hereinabove.

Generally the azetidinone sulfinamides and sulfinimides of this invention are prepared from the corresponding sulfinyl chlorides in the same manner carboxamides and carboximides are prepared from carboxylic acid chlorides; that is, by reacting the acid chloride with from about 1 to about 2 equivalents of an appropriate amine base. Typically this reaction, like the aforedescribed preparation of sulfinic acid esters and thioesters, is carried out in an inert organic solvent such as benzene, toluene, methylene chloride, chloroform, ethyl acetate or the like. The following table illustrates the particular bases employed to prepare individual sulfinamides and sulfinimides of this invention:

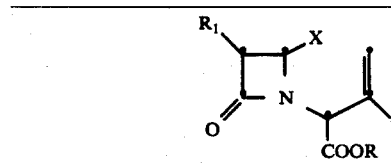

| X | Amine base |
|---|---|
| $-SNH_2$ with =O | $NH_4Cl$ |
| $-SNHR''$ with =O | $R''-NH_2$ |
| $-SNHNHCNH_2$ with two =O | $H_2NNHCNH_2$ with =O |
| $-SNHNHCNH(C_1-C_3)$alkyl with two =O | $H_2NNHCNH(C_1-C_3$alkyl) with =O |
| $-SNHNHCO(C_1-C_3$alkyl) with two =O | $H_2NNHCO(C_1-C_3$alkyl) with =O |
| $-SNHNHC(C_1-C_3$alkyl) with two =O | $H_2NNHC(C_1-C_3$alkyl) with =O |
| $-SNHNHS$—⟨phenyl⟩—$CH_3$ with three =O | $H_2NNHS$—⟨phenyl⟩—$CH_3$ with two =O |
| $-S-N$⟨imide with $R_2$⟩ with =O | $K^+ \ ^-N$⟨imide with $R_2$⟩ |

Succinimidosulfinyl azetidinones can also be prepared in accordance with the following reaction sequence.

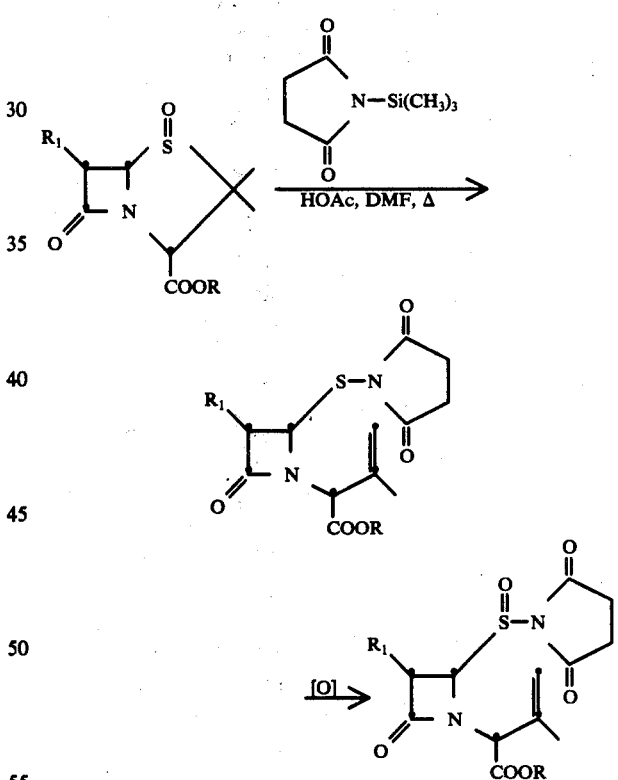

The penicillin sulfoxide ester is heated in dimethylformamide at about 105° C. with an excess of N-trimethylsilylsuccinimide in the presence of acetic acid. The azetidinone sulfenimide thereby derived [West German Patent No. DT2406165] is then oxidized with m-chloroperbenzoic acid to provide the corresponding sulfinimide derivative, a compound of the present invention.

Representative of the azetidinone sulfinamides and sulfinimides of the present invention are 4'-nitrobenzyl 3-methyl-2-(2-phthalimidosulfinyl-4-oxo-3-phenylacetamido-1-azetidinyl)-3-butenoate, 2'-iodoethyl 3-methyl-2-[2-(4-chloroanilinosulfinyl)-4-oxo-3-phenoxyacetamido-1-azetidinyl]-3-butenoate, benzhydryl 3-methyl-2-[2-carbamylhydrazosulfinyl-4-oxo-3-(4-nitrobenzyloxycarbonylamino)-1-azetidinyl]-3-butenoate, 4'-chlorophenacyl 3-methyl-2-(2-ethylcarbamylhydrazosulfinyl-4-oxo-3-formamido-1-azetidinyl)-3-butenoate, tert-butyl 3-methyl-2-[2-carboethoxyhydrazosulfinyl-4-oxo-3-(2-formyloxy-2-phenylacetamido)-1-azetidinyl]-3-butenoate, 2',2',2'-trichloroethyl 3-methyl-2-(2-propionylhydrazosulfinyl-4-oxo-3-phthalimido-1-azetidinyl)-3-butenoate, methyl 3-methyl-2-[2-(4-tolylsulfonylhydrazosulfinyl)-4-oxo-3-(2-chlorobenzamido)-1-azetidinyl]-3-butenoate, 4'-methoxybenzyl 3-methyl-2-(2-succinimidosulfinyl-4-oxo-3-propionamido-1-azetidinyl)-3-butenoate, 4'-nitrobenzyl 3-methyl-2-[2-(4-methoxyanilinosulfinyl)-4-oxo-3-phenoxyacetamido-1-azetidinyl]-3-butenoate, 2'-iodoethyl 3-methyl-2-[2-carbomethoxyhydrazosulfinyl-4-oxo-3-(2-thienylacetamido)-1-azetidinyl]-3-butenoate, and 2',2',2'-trichloroethyl 3-methyl-2-[2-acetylhydrazosulfinyl-4-oxo-3-(2-tert-butoxycarbonylamino-2-phenylacetamido)-1-azetidinyl]-3-butenoate.

In addition to the aforedescribed sulfinamides of the present invention, other sulfinamides can be employed as starting materials in the cyclization process of this invention. In particular, azetidinone sulfinamides of the formula

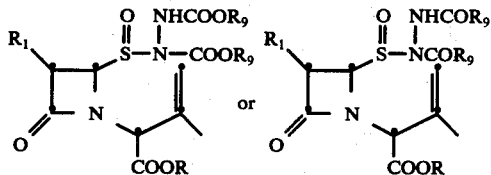

wherein R and $R_1$ are as defined hereinabove, and $R_9$ is $C_1$-$C_6$ alkyl or phenyl, can by cyclized under the acidic conditions of the present process to provide the corresponding 3-methylenecepham sulfoxides. Such azetidinone sulfinamides are known compounds. [S. Terao et al., supra]. They are prepared directly from penicillin sulfoxides by their reaction with azodicarboxylates or diacyldiimides. With the somewhat milder reaction conditions (verses those reaction conditions for sulfinyl halide preparation) for the preparation of these azetidinone sulfinamides, a wider range of penicillin sulfoxide starting materials may be employed.

Thus $R_1$ in the sulfinamide formula immediately hereinabove can represent, in addition to those groups described hereinbefore, an amide group of the formula

wherein R'''' is a heteroaryl group including among others 2-furyl, 3-furyl, 2-thiazoyl, or 4-isoxazolyl.

Exemplary of the sulfinamide starting materials derived directly from penicillin sulfoxides and azodicarboxylates or diacyldiimides, for the process of this invention are 4'-nitrobenzyl 3-methyl-2-[2-(N,N'-dicarbotertbutoxyhydrazosulfinyl)-4-oxo-3-(2-thienylacetamido)-1-azetidinyl]-3-butenoate, 2'-iodoethyl 3-methyl-2-[2-(N,N'-dibenzoylhydrazosulfinyl)-4-oxo-3-phenoxyacetamido-1-azetidinyl]-3-butenoate, 2',2',2'-trichloroethyl 3-methyl-2-[2-(N,N'-dicarboethoxyhydrazosulfinyl)-4-oxo-3-phenylacetamido-1-azetidinyl]-3-butenoate, benzhydryl 3-methyl-2-[2-(N,N'-dicarbomethoxyhydrazosulfinyl)-4-oxo-3-(2-formyloxy-2-phenylacetamido)-1-azetidinyl]-3-butenoate, and 4'-chlorophenacyl 3-methyl-2-[2-(N,N'-dicarbopropoxyhydrazosulfinyl)-4-oxo-3-acetamido-1-azetidinyl]-3-butenoate.

The scope of reagents suitable for effecting the intramolecular sulfinylation of the process of this invention is essentially coextensive with that of those reagents which have been recognized as capable of effectuating acylation reactions of the Friedel-Crafts type. An extensive survey of Friedel-Crafts acylations, related reactions, and catalysts therefor is presented by George A. Olah in "Friedel-Crafts Chemistry," John Wiley and Sons, New York, N.Y., 1973.

Suitable reagents which can be employed in the process of this invention to effect intramolecular cyclization of the aforedescribed azetidinone sulfinyl chlorides and sulfinyl bromides are the conventional Friedel-Crafts catalyst reagents, including Lewis acid type catalysts, Bronsted proton acid type catalysts, and metathetic cation-forming agents. Preferred of the Lewis acid type Friedel-Crafts catalysts are the metal halide Lewis acid type catalysts. The Bronsted proton acid type catalysts include acidic chalcides (particularly acidic oxides), conjugate Friedel-Crafts catalysts of the formula $HMA_{4,6}$, and both the organic and the inorganic Bronsted proton acids themselves.

Cyclization of the aforedescribed azetidinone sulfinic acids, esters, thioesters, amides, and imides, all compounds of this invention, is accomplished with Bronsted proton acid type catalysts.

The Lewis acid type catalysts are characterized by the presence of a vacant orbital which can accept an available electron pair, either unshared. e.g. on an oxygen, sulfur, or halide atom, or in a $\pi$ orbital, of a Lewis base type compound to form a covalent bond. Exemplary of suitable Lewis acid type metal catalysts are aluminum chloride, stannic chloride, stannic bromide, zinc chloride, zinc bromide, antimony pentachloride, titanium tetrachloride, ferric chloride, gallium trichloride, zirconium tetrachloride, mercuric chloride, chromium trichloride and like metal halide agents exhibiting Friedel-Crafts type catalytic activity. Preferred of such catalysts are stannic chloride, zinc chloride, zinc bromide, zirconium tetrachloride and titanium tetrachloride. Stannic chloride is most preferred.

The Bronsted proton acid type catalysts differ from the acidic halide Lewis acid type Friedel-Crafts catalysts in that, in the proton acid case, the electron acceptor quality is due to a positively charged entity, a proton. Exemplary of suitable organic Bronsted proton acid catalysts are methanesulfonic acid, ethanesulfonic acid, trifluoroacetic acid, trichloroacetic acid, dichloroacetic acid and like organic acid compounds. Suitable inorganic Bronsted proton acid catalysts for the process of this invention include sulfuric acid, phosphoric acid, polyphosphoric acid, perchloric acid, chlorosulfonic acid, fluorosulfonic acid and like proton acid catalysts. Preferred of the Bronsted proton acid catalysts are methanesulfonic acid, trifluoroacetic acid, phosphoric acid, sulfuric acid, and polyphosphoric acid.

The chalcide catalysts include a wide variety of solid oxides and sulfides. Olah, in "Friedel-Crafts Chemistry" supra, reported that as far as Friedel-Crafts acylations are concerned, acidic solid chalcide catalysts "seem to be the most attractive catalysts of the future." Of the acidic chalcides, acidic oxides or mixed acidic oxides are preferred for the process of this invention. Representative of such acidic oxides are alumina, silica, $Cr_2O_3$, $P_2O_5$, $TiO_2$, $Al_2O_3.CoO$ and $Al_2O_3.MnO$. Phosphorous pentoxide is most preferred. Generally for Friedel-Crafts acylations dehydrated chalcides are inactive as catalysts; the addition of small amounts (about 1-5% by weight) of water, however, activates the catalytic activity of these catalysts. Absorbed protons seem to be essential to the catalytic activity of acid chalcide catalysts. The effect of water suggests that Bronsted acidity is responsible for the catalyst activity of the acid chalcides [F. E. Condon in "Catalysts," Vol. VI, ed. P. H. Emmet, Reinhold Publ. Corp., New York, N.Y. (1953), p 43]. Thus for the purpose of this invention acid chalcides are classified as Bronsted proton type catalysts.

It should also be noted that, as is sometimes the case in Friedel-Crafts type acylations, a metal halide Lewis acid catalyst can be used in conjunction with a Bronsted proton acid catalyst, the effective catalyst agent being a conjugate Friedel-Crafts acid catalyst of the type $HMA_{4,6}$. Bronsted acid type activity is presumed to be responsible for the effectiveness of this type of catalyst reagent. Thus, for the purpose of this invention it is intended that such conjugate catalysts be classified as Bronsted type catalysts. Exemplary of such conjugate acid catalysts are $HBF_4$, $HAlCl_4$, $HAsF_6$, and $HAlBr_4$.

Although their activity in the real sense is not catalytic (because they are generally consumed in the cation-forming reaction), metathetic cation-forming agents, particularly anhydrous silver salts, such as silver p-toluenesulfonate, silver perchlorate, silver phosphate, silver tetrafluoroborate, silver trifluoroacetate and like silver compounds are effective "catalysts" in the Friedel-Crafts type cyclization of azetidinone sulfinyl halides in the process of this invention. These silver salts act as metathetic cation-forming substances when reacted with halide reagents and not as acids. Thus the proposed intermediate sulfinium type cation is generated from the sulfinyl chloride by chloride abstraction with the silver cation and not by an acid-base type reaction as is the case with the aforedescribed acid catalyst reagents. The insoluble by-product silver chloride precipitates. Silver p-toluenesulfonate is a preferred metathetic cation-forming agent for the process of this invention.

The metathetic cation-forming agents are effective only with azetidinone sulfinyl halide starting materials; such reagents are not suitable for the cyclization of any of the other corresponding sulfinic acid derivatives of this invention. Such other sulfinic acid derivatives of this invention are cyclized using a Bronsted proton acid type catalyst.

The azetidinone sulfinyl halide starting materials for the process of the present invention can thus be cyclized by their reaction with a Lewis acid type metal halide catalyst, a Bronsted proton acid type catalyst, or a metathetic cation-forming agent. The best yields of 3-methylene cepham sulfoxides from azetidinone sulfinyl chlorides, preferred starting materials for the process of this invention, are achieved when Lewis acid type metal halide catalysts are employed. However, good yields of the product sulfoxides from sulfinyl halide starting materials have been achieved with Bronsted proton acid type catalysts and metathetic cation-forming agents. Lewis acid type metal halide catalysts are preferred in the process of the present invention when azetidinone sulfinyl chlorides and sulfinyl bromides are employed as starting materials. Bronsted proton acid type catalysts are preferred in the process of this invention when the azetidinone sulfinic acids, and the corresponding sulfinate esters, thiosulfinate esters, sulfinamides and sulfinimides, compounds of the present invention, are employed as starting materials.

Any of a wide variety of dry inert organic solvents may be employed as the medium for the cyclization process of this invention. By "inert organic solvent" is meant an organic solvent which, under the conditions of the process, does not enter into any appreciable reaction with either the reactants or the products. Since the sulfinyl chloride starting materials, like other acid halide type reagents, are susceptible to hydrolysis and to attack by other protic compounds, e.g. alcohols and amines, moisture and other such protic compounds in the reaction medium should be rigorously excluded. A dry aprotic organic solvent is thus preferred. Trace amounts of water such as that found in commercially dried solvents, can be tolerated; however, it is generally preferred that the process of this invention be carried out under anhydrous conditions. Suitable solvents include, for example, aromatic hydrocarbons, such as, benzene, toluene, xylene, chlorobenzene, nitrobenzene, nitromesitylene and the like; halogenated aliphatic hydrocarbons, such as chloroform, methylene chloride, carbon tetrachloride, 1,2-dichloroethane (ethylene chloride), 1,1,2-trichloroethane, 1,1-dibromo-2-chloroethane; and other solvents recognized by those skilled in the art as suitable for Friedel-Crafts type reactions, including among others, carbon disulfide and nitromethane. The preferred solvents are aromatic hydrocarbons and halogenated aliphatic hydrocarbons. Most preferred aromatic hydrocarbon solvents are benzene and toluene. Most preferred of the halogenated aliphatic hydrocarbons are methylene chloride, ethylene chloride, and 1,1,2-trichloroethane.

The temperature at which the process of the present invention is carried out is dependent on the particular catalyst or agent employed; the temperature must be sufficient to effect the cyclization of the starting material. It is well known by those skilled in the art that different Friedel-Crafts reagents are effective at different temperatures in accomplishing, for example, a given acylation. Moreover, such is known to be true even within a particular class of Friedel-Crafts reagents. The process of the present invention can be carried out generally at a temperature ranging from 5° to 150° C.

The cyclization of both the azetidinone sulfinic acid derivatives of this invention and the sulfinyl halides can be carried out with Bronsted proton acid type catalysts in an inert organic solvent at a temperature of about 70° to about 115° C., typically the reflux temperature of the medium in which the cyclization is being carried out.

Alternatively, any one of the aforedescribed azetidinone sulfinyl derivatives can be cyclized to the corresponding exomethylenecepham sulfoxide by its dissolution in a neat organic Bronsted proton acid such as methanesulfonic acid, trifluoromethanesulfonic acid, trifluoroacetic acid, trichloroacetic acid or dichloroacetic acid. The time required for cyclization under such conditions is dependent upon the nature of the sulfinyl derivative, the particular acid employed and the temperature of the reaction. Typically azetidinone sulfinamide and sulfinimide derivatives are cyclized within 5 to 10 minutes at room temperature in methane sulfonic acid while cyclization of the sulfinic acids, esters, and thioester derivatives thereof, is complete after about 30 minutes at room temperature.

The cyclization of the aforedescribed azetidinone sulfinyl halides is preferably carried out at a temperature ranging from about 10° to about 115° C. More preferably the reaction is accomplished at a temperature between about 20° and about 85° C., the most preferred temperature being dependent primarily upon the solubility and the catalytic activity of the particular cyclizing agent employed. When a Bronsted proton acid type catalyst (including acid chalcide catalysts and conjugate Friedel-Crafts acid catalysts) is employed as the catalyst reagent to cyclize a sulfinyl halide derivative in an inert organic solvent, the preferred reaction temperature ranges from about 70° to about 115°, typically the reflux temperature of the medium in which the cyclization is being carried out. However, cyclization of methyl 3-methyl-2-(2-chlorosulfinyl-4-oxo-3-phthalimido-1-azetidinyl)-3-butenoate was effected in neat polyphosphoric acid at room temperature. The intramolecular sulfinylation, when effected by a metathetic cation-forming agent, is preferably carried out at a temperature between about 20° and about 80°; most preferred is room temperature. When a metal halide Lewis acid type catalyst, preferred for the cyclization of the sulfinyl halides, is employed, the preferred temperature at which the process can be carried out is particularly dependent on the individual metal halide catalyst reagent. Thus, when stannic chloride, stannic bromide or antimony pentachloride, which reagents are usually soluble in the solvents for the process, are employed, the cyclization is carried out preferably at a temperature from about 10° to about 40° C.; the most preferred temperature when such reagents are used is about room temperature. However, when titanium tetrachloride, a liquid which is also soluble in most of the reaction solvents, is employed, an elevated temperature of about 40° to about 100° is preferred for the conversion. When metal halide Lewis acid type catalysts, other than those few specifically referred to immediately hereinabove, are employed in the process of this invention, an elevated temperature of about 40° to about 115° is generally preferred; a temperature of about 40° to about 85° is most preferred.

When stannic chloride is employed as the cyclizing agent in the process of the present invention in a toluene medium, an intermediate stannic chloride-sulfinyl halide complex can be isolated simply by filtering the reaction mixture. The complex can be dried and stored or it can be dissolved in ethyl acetate and washed successively with hydrochloric acid, water, and brine to provide the corresponding exomethylenecepham sulfoxide.

In order to ensure completion of the cyclization reaction of a sulfinyl halide, at least a stoichiometric (mole per mole) amount of a Lewis acid type Friedel-Crafts catalyst or of a metathetic cation-forming agent is employed. Using less than one molar equivalent of such reagents results in lower yields of the product 3-methylenecepham sulfoxide and leaves a portion of the sulfinyl chloride unreacted. Typically the amount of catalyst reagent employed will range from slightly over one equivalent to about two equivalents per mole of sulfinyl chloride. Preferably about 1.1 equivalents of metal halide Lewis acid or of metathetic cation-forming agent are employed for each mole of azetidinone sulfinyl halide starting material. Although less than a stoichiometric amount of a Bronsted proton acid type Friedel-Crafts catalyst can be employed to effect complete cyclization of either a sulfinyl chloride or other sulfinic acid derivative, approximately an equivalent amount or more of such acid catalysts is typically employed. As stated hereinabove, the cyclization can also be effected in a neat protic acid; such is a preferred method.

The time of the reaction under the aforedescribed conditions will range generally from 5 minutes to about 2 hours with the reaction time being dependent to some extent upon the particular reactants, the solvents employed and the temperature at which the reaction is carried out. Usually, the reaction will be completed after the reactants have been maintained in contact at the preferred temperatures for about 45 to 90 minutes; however, as indicated hereinabove, shorter reaction times are appropriate under certain conditions. The reaction mixture can easily be monitored for example, by comparative thin-layer chromatography, to determine when the cyclization reaction has reached completion.

The mechanism by way of which the process of the present invention accomplishes the desired results has not been established with certainty, but the intermediacy of a sulfinium ion (Formula I)

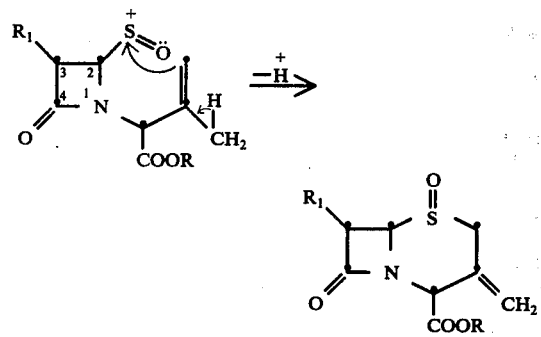

or a complex thereof, wherein the C-2 substituent on the azetidinone ring is

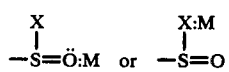

(M = H+ or metal halide Lewis acid) is highly probable. Cyclization of the deuterated sulfinyl chloride of Formula II, prepared from methyl 6-phthalimido -continued

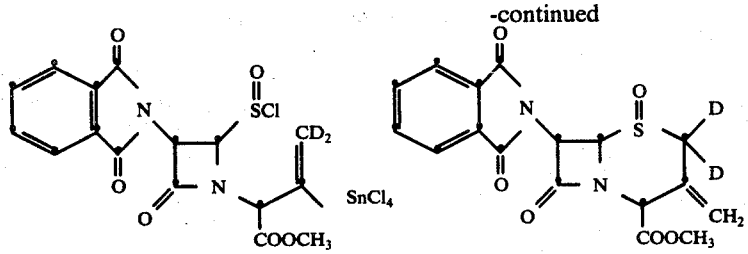

3β-methyl-3α-trideuteriomethylpenam-3-carboxylate 1α-oxide [R.D.G. Cooper, *Journal of the American Chemical Society,* 92, 5010 (1970)], with stannic chloride provided methyl 7-phthalimido-2,2-dideuterio-3-methylenecepham-4-carboxylate 1-oxide.

The following are representative of the conversions which can be accomplished by the process of the present invention:

tert-Butyl 3-methyl-2-(2-chlorosulfinyl-4-oxo-3-phthalimido-1-azetidinyl)-3-butenoate, derived from tert-butyl 6-phthalimidopenicillanate sulfoxide, is cyclized to 7-phthalimido-3-methylenecepham-4-carboxylic acid sulfoxide;

Benzyl 3-methyl-2-(2-chlorosulfinyl-4-oxo-3-benzyloxycarbonylamino-1-azetidinyl)-3-butenoate, derived from benzyl 6-benzyloxycarbonylamino penicillanate sulfoxide, is cyclized to benzyl 7-benzyloxycarbonylamino-3-methylenecepham-4-carboxylate sulfoxide;

4'-Methoxybenzyl-3-methyl-2-(2-sulfino-4-oxo-3-phenoxyacetamido-1-azetidinyl)-3-butenoate, derived from 4'-methoxybenzyl 6-phenoxyacetamidopenicillanate sulfoxide, is cyclized to 7-phenoxyacetamido-3-methylenecepham-4-carboxylic acid sulfoxide;

2',2',2'-Trichloroethyl 3-methyl-2-(2-chlorosulfinyl)-4-oxo-3-phenylthioacetamido-1-azetidinyl)-3-butenoate, derived from 2',2',2'-trichloroethyl 6-phenylthioacetamidopenicillanate sulfoxide, is cyclized to 2',2',2'-trichloroethyl 7-phenylthioacetamido-3-methylenecepham-4-carboxylate sulfoxide;

4'-Nitrobenzyl 3-methyl-2-[2-(N,N'-di(carbomethoxy)hydrazosulfinyl)-4-oxo-3-(2-thienylacetamido)-1-azetidinyl]-3-butenoate, derived from 4'-nitrobenzyl 6-(2-thienylacetamido)penicillanate sulfoxide, is cyclized to 4'-nitrobenzyl 7-(2-thienylacetamido)-3-methylenecephem-4-carboxylate sulfoxide;

Benzhydryl 3-methyl-2-(2-chlorsulfinyl-4-oxo-3-(2,2-dimethyl-3-nitroso-5-oxo-4-phenyl-1-imidazolidinyl)-1-azetidinyl]-3-butenoate, derived from benzhydryl 6-(2,2-dimethyl-3-nitroso-5-oxo-4-phenyl-1-imidazolidinyl)penicillanate sulfoxide [hetacillin benzhydryl ester], is cyclized to 7-(2,2-dimethyl-3-nitroso-5-oxo-4-phenyl-1-imidazolidinyl)-3-methylenecepham-4-carboxylic acid sulfoxide;

2'-Iodoethyl 3-methyl-2-(2-sulfino-4-oxo-3-chloroacetamido-1-azetidinyl)-3-butenoate, derived from 2'-iodoethyl 6-chloroacetamidopenicillanate sulfoxide, is cyclized to 2'-iodoethyl 7-chloroacetamido-3-methylenecepham-4-carboxylate sulfoxide;

Dimethylallyl 3-methyl-2-(2-chlorosulfinyl-4-oxo-3-maleimido-1-azetidinyl)-3-butenoate, derived from dimethylallyl 6-maleimidopenicillanate sulfoxide, is cyclized to dimethylallyl 7-maleimido-3-methylenecepham-4-carboxylate sulfoxide;

Succinimidomethyl 3-methyl-2-(2-chlorosulfinyl-4-oxo-3-cyanoacetamido-1-azetidinyl)-3-butenoate, derived from succinimidomethyl 6-cyanoacetamidopenicillanate sulfoxide, is cyclized to succinimidomethyl 7-cyanoacetamido-3-methylenecephem-4-carboxylate sulfoxide;

4'-Nitrobenzyl 3-methyl-2-[2-sulfino-4-oxo-3-(4-nitrobenzyloxycarbonylamino)-1-azetidinyl]-3-butenoate, derived from 4'-nitrobenzyl 6-(4-nitrobenzyloxycarbonylamino)penicillanate sulfoxide, is cyclized by 4'-nitrobenzyl 7-(4-nitrobenzyloxycarbonylamino)-3-methylenecepham-4-carboxylate sulfoxide;

4'-Nitrobenzyl 3-methyl-2-[2-chlorosulfinyl-4-oxo-3-(2-thienylacetamido)-1-azetidinyl]-3-butenoate, derived from 4'-nitrobenzyl 7-(2-thienylacetamido)penicillanate sulfoxide, is cyclized to 4'-nitrobenzyl 7-2-thienylacetamido)-3-methylenecephem-4-carboxylate sulfoxide;

Benzhydryl 3-methyl-2-[2-chlorosulfinyl-4-oxo-3-(2-tert-butoxycarbonylamino-2-phenylacetamido)-1-azetidinyl]-3-butenoate, derived from benzhydryl 6-(2-tert-butoxycarbonylamino-2-phenylacetamido)penicillanate sulfoxide, is cyclized to 7-(2-amino-2-phenylacetamido)-3-methylenecepham-4-carboxylic acid sulfoxide;

4'-Methoxybenzyl 3-methyl-2-[2-chlorosulfinyl-4-oxo-3-(2-benzyloxy-2-phenylacetamido)-1-azetidinyl]-3-butenoate, derived from 4'-methoxybenzyl 6-(2-benzyloxy-2-phenylacetamido)penicillanate sulfoxide, is cyclized to 7-(2-benzyloxy-2-phenylacetamido)-3-methylenecepham-4-carboxylic acid sulfoxide;

2',2',2'-Trichloroethyl 3-methyl-2-[2-chlorosulfinyl-4-oxo-3-(2-benzyloxy-2-phenylacetamido)-1-azetidinyl]-3-butenoate, derived from 2',2',2'-trichloroethyl 6-(2-benzyloxy-2-phenylacetamido)penicillanate sulfoxide, is cyclized to 2',2',2'-trichloroethyl 7-(2-benzyloxy-2-phenylacetamido)-3-methylenecephem-4-carboxylate sulfoxide;

4'-Nitrobenzyl 3-methyl-2-(2-isoproxysulfinyl-4-oxo-3-benzamido-1-azetidinyl)-3-butenoate, derived from 4'-nitrobenzyl 6-benzamidopenicillanate sulfoxide, is cyclized to 4'-nitrobenzyl 7-benzamido-3-methylenecepham-4-carboxylate sulfoxide;

2'-Iodoethyl 3-methyl-2-(2-cyclohexyloxysulfinyl-4-oxo-3-chloroacetamido-1-azetidinyl)-3-butenoate, derived from 2'-iodoethyl 6-chloroacetamidopenicillanate sulfoxide, is cyclized to 2'-iodoethyl 7-chloroacetamido-3-methylenecepham-4-carboxylate sulfoxide;

2',2',2'-Trichloroethyl 3-methyl-2-[2-N,N'-di(carboethoxy)hydrazosulfinyl-4-oxo-3-(2-thienylacetamido)-1-azetidinyl]-3-butenoate, derived from 2',2',2'-trichloroethyl 6-(2-thienylacetamido)penicillanate sulfoxide, is cyclized to 2',2',2'-trichloroethyl 7-(2-thienylacetamido)-3-methylenecepham-4-carboxylate sulfoxide;

Methyl 3-methyl-2-[2-carbamylhydrazosulfinyl-4-oxo-3-(3-nitrophenoxyacetamido)-1-azetidinyl]-3-butenoate, derived from methyl 6-(3-nitrophenoxyacetamido)penicillanate sulfoxide, is cyclized to methyl 7-(3-nitrophenoxyacetamido)-3-methylenecepham-4-carboxylate sulfoxide;

Benzhydryl 3-methyl-2-[2-(4-chloroanilinosulfinyl)-4-oxo-3-(4-nitrobenzyloxycarbonylamino)-1-azetidinyl]-3-butenoate, derived from benzhydryl 6-(4-nitrobenzyloxycarbonylamino) pencillanate sulfoxide is cyclized to 7-(4-nitrobenzyloxycarbonylamino)-3-methylenecepham-4-carboxylic acid sulfoxide;

4'-Nitrobenzyl 3-methyl-2-(2-phthalimidosulfinyl-4-oxo-3-phenylacetamido-1-azetidinyl)-3-butenoate derived from 4'-nitrobenzyl 6-phenylacetamidopenicillanate sulfoxide, is cyclized to 4'-nitrobenzyl 7-penylacetamido-3-methylene-cepham-4-carboxylate sulfoxide;

2'-Iodethyl 3-methyl-2-(2-bromosulfinyl-4-oxo-3-phthalimido-1-azetidinyl)-3-butenoate, derived from 2'-iodoethyl 6-phthalimidopenicillinate sulfoxide, is cyclized to 2'-iodoethyl 7-phthalimido-3-methylenecepham-4-carboxylate sulfoxide;

4'-Nitrobenzyl 3-methyl-2-(2-phenylthiosulfinyl-4-oxo-3-phenoxyacetamido-1-azetidinyl)-3-butenoate, derived from 4'-nitrobenzyl 6-phenoxyacetamidopenicillanate sulfoxide, is cyclized to 4'-nitrobenzyl 7-phenoxyacetamido-3-methylenecepham-4-carboxylate sulfoxide;

Phenacyl 3-methyl-2-[2-(2-phenylethylthiosulfinyl)-4-oxo-3-(2-benzyloxy-2-phenylacetamido)-1-azetidinyl]-3-butenoate derived from phenacyl 6-(2-benzyloxy-2-phenylacetamido) penicillanate sulfoxide, is cyclized to phenacyl 7-(2-benzyloxy-2-phenylacetamido)-3-methylenecepham-4-carboxylate sulfoxide;

tert-Butyl 3-methyl-2-[2-methylcarbamylhydrazo-sulfinyl-4-oxo-3-(4-methoxyphenylacetamido)-1-azetidinyl]-3-butenoate, derived from tert-butyl 6-(4-methoxyphenylacetamido)penicillanate sulfoxide, is cyclized to 7-(4-methoxyphenylacetamido)-3-methylenecepham-4-carboxylic acid sulfoxide;

Trimethylsilyl 3-methyl-2-(2-carbomethoxyhydrazosulfinyl-4-oxo-3-phenylacetamido-1-azetidinyl)-3-butenoate, derived from timethylsilyl 6-phenylacetamidopenicillanate sulfoxide, is cyclized to 7-phenylacetamido-3-methylenecepham-4-carboxylic acid sulfoxide; and 4'-chlorophenacyl 3-methyl-2-[2-(2-chloroethoxysulfinyl)-4-oxo-3-formamido-1-azetidinyl]-3-butenoate, derived from 4'-chlorophenacyl 6-formamidopenicillanate sulfoxide, is cyclized to 4'-chlorophenacyl 7-formamido-3-methylenecepham-4-carboxylate sulfoxide.

The yield of the products will vary depending upon the particular reactants which are employed, the relative quantities of reagents and the other aforementioned conditions of reaction.

The products produced in accordance with the process of this invention can be isolated and purified by employing conventional experimental techniques. These include chromatographic separation, filtration, crystallization, recrystallization and like methods.

Preferred side chains, $R_1$ in the above formulae, for the present invention are those side chains found on penicillins produced directly by fermentation, primarily the phenylacetamido and phenoxyacetamido side chains. Another preferred side chain of this same class is the 2-thienylacetamido side chain. The penicillins can be esterified and oxidized (not necessarily in that order) to the respective penicillin sulfoxide esters from which the sulfinyl chloride intermediates, and other starting materials for the process of the present invention, are derived. It should be noted that the aforementioned preferred side chains are so preferred primarily for economic reasons. Penicillin precursors having such side chains are readily available and relatively inexpensive; the advantage of performing the process of this invention with the aforedescribed sulfinyl intermediates derived therefrom is readily discernible. Of course, penicillin sulfoxides bearing other known side chains may easily be prepared (by acylation of 6-APA or 6-APA esters and subsequent oxidation) and employed in the process of the present invention. It is not intended that the present invention be limited by the acylamino groups specifically disclosed herein.

The product 3-methylenecepham sulfoxides of the process of this invention are useful as intermediates in the preparation of antibiotic compounds. The sulfoxides can be reduced by known procedures, typically with phosphorous trichloride or phosphorous tribromide in dimethylformamide, to provide the corresponding 3-methylenecephams which are predictably converted in high yield to desacetoxycephalosporins of the formula

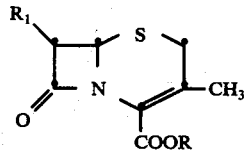

upon treatment with triethylamine in dimethylacetamide. [Robert R. Chauvette and Pamela A. Pennington, J. Org. Chem., 38, 2994 (1973).]. The desacetoxycephalosporin esters are converted to active antibiotics by cleavage of the ester function. Deesterification can be achieved, depending on the nature of the protecting group, by any one of several recognized procedures, including (1) treatment with an acid such as trifluoroacetic acid, formic acid, hydrochloric acid or the like; (2) treatment with zinc and an acid such as formic acid, acetic acid or hydrochloric acid; or (3) hydrogenation in the presence of palladium, platinum, rhodium or a compound thereof, in suspension, or on a carrier such as barium sulfate, carbon, alumina or the like.

Alternatively the exomethylenecephams can be employed in the preparation of novel cephem antibiotics of the formula

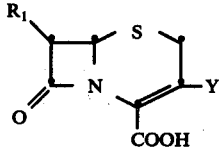

wherein Y, is, for example, chloro, bromo or methoxy. Such chemical conversions of 3-exomethylenecepham compounds have been disclosed in the chemical literature [Robert R. Chauvette and Pamela A. Pennington, Journal of the Americal Chemical Society, 96, 4986 (1974)].

In general, the exomethylenecepham compounds are converted by low temperature ozonolysis to 3-hydroxycephems which are in turn treated with diazomethane in methylene chloride/ether at room temperature to afford the 3-methoxycephem derivatives. The 3-halocephems are derived from the 3-hydroxycephem esters by treatment with a halogenating reagent such as thionyl chloride or phosphorous tribromide in dimethylformamide. The corresponding cephem acids exhibit potent antibacterial activity.

The following examples are provided to further illustrate the present invention. It is not intended that this invention be limited in scope by reason of any of these examples. In the following examples and preparations nuclear magnetic resonance spectra are abbreviated nmr. The nuclear magnetic resonance spectra were obtained on a Varian Associates T-60 Spectrometer using tetramethylsilane as the reference standard. The chemical shifts are expressed in δ values in parts per million (ppm) and coupling constants (J) are expressed as Hz in cycles per second.

EXAMPLE 1

Methyl 7-Phthalimido-3-methylenecepham-4-carboxylate-1-oxide

A. Stannic Chloride

A mixture of 18.8 g (50 mmol.) of methyl 6-phthalimidopenicillanate sulfoxide and 6.7 g. (50 mmol.) of N-chlorosuccinimide in 1 l. of dry carbon tetrachloride was refluxed for 70 min. The crude product was cooled to room temperature, filtered, washed with water (1 × 500 ml.), and dried (MgSO$_4$). The solvent was then evaporated in vacuo to dryness. The nmr spectrum indicated a complete conversion to the sulfinyl chloride; nmr (CDCl$_3$) δ1.97 (broad s, 3), 3.86 (s, 3), 5.05 (br. s, 2), 5.2 (d, 1, J=2 Hz), 5.77 (d, 1, J=4 Hz), 5.9 (d, 1, J=4 Hz), and 7.83 (m, 4). The product sulfinyl chloride was then dissolved in 1 l. of dry CH$_2$Cl$_2$ and 6 ml. (50 mmol.) of anhydrous stannic chloride was added. The resulting solution was stirred for 45 min., washed with 1N, hydrochloric acid (2 × 200 ml.), and dried (MgSO$_4$). Evaporation in vacuo gave 18.4 g. (98.4%) of a mixture of R- and S-sulfoxides (ca. 3:2 by nmr) as a light yellow foam. A portion of this mixture (1.26 g.) was separated by chromatography over silica gel using chloroform/ethyl acetate as a solvent. Fractions 6–10 contained pure R-sulfoxide (340 mg.) which was recrystallized from methylene chloride/cyclohexane (m.p. 201°–202°); nmr (CDCl$_3$) δ3.62 and 4.12 (ABq, 2, J=14 Hz), 3.85 (s, 3), 4.88 (d, 1, J=4.5 Hz), 5.25 (br. s, 1), 5.58 (m, 2), 5.97 (d, 1, J=4.5 Hz), and 7.84 (m, 4); mass spectrum m/e 374, 358, 346, 298, 287, 239, 220; ir (KBr): 1780, 1745, and 1390 cm$^{-1}$.

Anal. Calcd. for C$_{17}$H$_{14}$N$_2$O$_6$S (374.37): C, 54.54; H, 3.77; N, 7.48; O, 25,64; S, 8.56.

Found: C, 54.41; H, 4.06; N, 7.26; O, 25.59; and S, 8.41.

Fractions 11–18 contained a mixture of the R- and S-sulfoxides and fractions 19–35 gave 210 mg. of the S-sulfoxide, which was recrystallized from methylene chloride/cyclohexane; nmr (CDCl$_3$) δ3.63 (s, 2), 3.82 (s, 3), 4.90 (d, 1, J=4.5 Hz), 5.32 (s, 1), 5.46 (br. s, 1), 5.64 (d, 1, J=4.5 Hz), 5.77 (s, 1), and 7.84 (m, 4); mass spectrum m/e 374, 358, 346, 298, 287, 239, 200; ir (KBr) 1775, 1745, 1725, 1390, 1205, 1111, 1051, 730, and 715 cm$^{-1}$.

Anal. Calcd. for C$_{17}$H$_{14}$N$_2$O$_6$S: C, 54.54; H, 3.77; N, 7.48.

Found: C, 54.33; H, 3.76; N, 7.36.

B. Titanium tetrachloride

A solution of 0.41 g. of methyl 3-methyl-2-(2-chlorosulfinyl-4-oxo-3-phthalimido-1-azetidinyl)-3-butenoate and 0.12 ml. of titanium tetrachloride in 30 ml. of dry 1,2-dichloroethane was refluxed for 30 minutes. The mixture was then cooled to room temperature, washed with 1N.HCl and brine and dried (MgSO$_4$). Evaporation in vacuo to dryness provided 0.34 g. of methyl 7-phthalimido-3-methylenecepham-4-carboxylate 1-oxide.

C. Aluminum Chloride.

A mixture of 0.41 g. of methyl 3-methyl-2-(2-chlorosulfinyl-4-oxo-3-phthalimido-1-azetidinyl)-3-butenoate and 0.13 g. of aluminum chloride was refluxed in 30 ml. of dry 1,2-dichloroethane. The mixture was then cooled to room temperature, washed with 1N.HCl and brine and dried (MgSO$_4$). Evaporation in vacuo to dryness provided 0.35 g. of the 3-methylene cepham sulfoxide as a yellow foam.

D. Zinc bromide.

A mixture of 0.41 g. of methyl 3-methyl-2-(2-chlorosulfinyl-4-oxo-3-phthalimido-1-azetidinyl)-3-butenoate and 0.27 g. of zinc bromide in 30 ml. of dry methylene chloride was refluxed for 1 hour. The mixture was cooled to room temperature, washed with 1N.HCl and dried (MgSO$_4$). Evaporation in vacuo to dryness provided a mixture of the R- and S-3-methylenecepham sulfoxide as a yellow foam.

E. Antimony pentachloride.

A solution of 0.41 g. of methyl 3-methyl-2-(2-chlorosulfinyl-4-oxo-3-phthalimido-1-azetidinyl)-3-butenoate and 0.12 ml. of antimony pentachloride was stirred at room temperature for 60 minutes. The reaction mixture was washed with 1N.HCl and brine, dried (MgSO$_4$) and evaporated in vacuo to dryness to provide the desired 3-methylenecepham sulfoxide as a yellow foam. The nmr spectrum of the product sulfoxide mixture was poor. To confirm the presence of the cepham sulfoxide, the reaction product was dissolved in 3 ml. of dimethylformamide and reacted with 0.09 ml. of phosphorous trichloride. After the mixture was stirred at 0° for 30 minutes, it was poured over cracked ice/water. The yellow precipitate which then formed was collected by filtration and dried under vacuum. An nmr spectrum of the product (0.15 g.) showed it to be methyl 7-phthalimido-3-methylenecepham-4-carboxylate: (CDCl$_3$) δ3.47, 3.96 (ABq, 2, J=17 Nz, C$_2$—H), 3.87 (s, 3, C$_4$—H), 5.20 (d, 1, J=4.5 Hz), 5.80 (d, 1, J=4.5 Hz), and 7.83 (m, 4).

F. Mercuric chloride.

A mixture of 0.20 g. of methyl 3-methyl-2-(2-chlorosulfinyl-4-oxo-3-phthalimido-1-azetidinyl)-3-butenoate and 0.14 g. of mercuric chloride in 10 ml. of dry 1,2-dichloroethane was refluxed for 1 hour. The mixture was cooled to room temperature, washed with 1N.HCl, dried (MgSO$_4$) and evaporated in vacuo to dryness to provide 0.14 g. of 3-methylenecepham sulfoxide as a mixture of R- and S-sulfoxide isomers.

G. Ferric chloride.

The same procedure was followed as in (F) above with the exception that 0.08 g. of ferric chloride was employed as the catalyst instead of mercuric chloride. Comparative thin-layer chromatography confirmed the sulfinyl chloride to 3-methylenecepham sulfoxide conversion.

H. Zirconium tetrachloride.

The same procedure was followed as in (F) above with the exception that 0.12 g. of zirconium tetrachloride was employed as the catalyst instead of mercuric chloride. Comparative thin-layer chromatography confirmed a clean conversion to the sulfinyl chloride to the 3-methylenecepham sulfoxide. The nmr spectrum of the product was identified to that of the product in (A) above.

I. Polyphosphoric acid.

Methyl 3-methyl-2-(2-chlorosulfinyl-4-oxo-3-phthalimido-1-azetidinyl)-3-3-butenoate (0.20 g.) was stirred in about 27 g. of polyphosphoric acid for 20 minutes. Ice water and ethyl acetate (25 ml.) was added to the reaction mixture. The organic layer was separated and washed successively with water, aqueous sodium bicarbonate, and brine, dried (MgSO$_4$), and evaporated in vacuo to dryness to give methyl 7-phthalimido-3-methylenecepham-4-carboxylate 1-oxide (0.05 g.) as a white foam.

J. Sulfuric acid.

A solution of 0.20 g. of methyl 3-methyl-2-(2-chlorosulfinyl-4-oxo-3-phthalimido-1-azetidinyl)-3-butenoate and 2 drops of concentrated sulfuric acid in 10 ml. of dry 1,2-dichloroethane was refluxed for 1 hour. The reaction mixture was cooled, washed with brine, dried (MgSO$_4$) and evaporated in vacuo to dryness to provide 0.09 g. of a colorless foam, the nmr spectrum of which shows it to be primarily the desired 3-methylenecepham sulfoxide.

K. Methanesulfonic acid.

The same procedure was followed as in (I) above with the exception that 0.03 ml. of methanesulfonic acid was employed as the catalyst instead of sulfuric acid. The product, as identified by nmr spectroscopy, was the desired 3-methylenecepham sulfoxide.

L. Trifluoroacetic acid.

A solution of 0.29 g. of methyl 3-methyl-2-(2-chlorosulfinyl-4-oxo-3-phthalimido-1-azetidinyl)-3-butenoate in 10 ml. of trifluoroacetic acid was refluxed for 30 minutes and then was evaporated in vacuo to dryness. The product was dissolved in 20 ml. of ethyl acetate. The resulting solution was washed successively with aqueous sodium bicarbonate (3X), water, and brine, dried (MgSO$_4$), and evaporated in vacuo to dryness to provide methyl 7-phthalimido-3-methylenecepham-4-carboxylate 1-oxide.

M. Silver p-toluenesulfonate

Silver p-toluenesulfonate (0.80 g.) was added to a solution of 1.0 g. of methyl 3-methyl-2-(2-chlorosulfinyl-4-oxo-3-phthalimido-1-azetidinyl)-3-butenoate in 75 ml. of dry toluene. The reaction mixture was stirred at room temperature for 2.5 hours and then filtered. The filtrate was evaporated in vacuo to dryness, and the residue thereby obtained was dissolved in 50 ml. ethyl acetate. The solution was washed in vacuo to dryness. The product was identified by nmr spectroscopy as methyl 7-phthalimido-3 methylenecepham-4-carboxylate 1-oxide.

EXAMPLE 2

Methyl 7-phthalimido-2,2-dideuterio-3-methylenecepham-4-carboxylate

A mixture of 3.76 g. (10 mmol) of methyl 6$\beta$-phthalimidopenicillanate sulfoxide, 5 ml. deuterium oxide, and 500 ml. dry carbon tetrachloride was refluxed for 3 hr. The layers were then separated and organic layer dried (MgSO$_4$). Evaporation in vacuo gave 3.59 g. of a white amorphous foam. The nmr spectrum showed deuterium (H$^2$) incorporation into the 2$\alpha$-methyl group only and the residual hydrogen (H$^1$) in that group of less than 29% (by integration). Mass spectral analysis gave the following deuterium distribution in the 2$\alpha$-methyl group: d$_0$, 5.8%; d$_1$, 20.5%; d$_2$, 41.3%; d$_3$, 32.4% ± 2%. Recrystallization from acetone/diethyl ether gave colorless prisms, mp 148°–151°; mass spectrum, m/e 379, 378, 377, 376, 361, 360, 359, 358, 302,/301, 300, 299; ir (KBr) 1800, 1775, and 1725 cm$^{-1}$; nmr (CDCl$_3$) $\delta$1.83 (s, 3); 3.85 (s, 3); 4.62 (s, 1); 4.85 (d, 1, J=4.5 Hz), 5.86 (d, 1, J=4.5 Hz); 7.83 (m, 4).

Anal. Calcd. for C$_{17}$H$_{16}$N$_2$O$_6$S (376.387): C, 54.25; H, 4.28; N, 7.44; O, 25.50; S, 8.52.

Found: C, 54.05; H, 4.28; N, 7.26; O, 25.61; S, 8.53.

A solution of 0.57 g. (1.5 mmol.) of the methyl 2$\beta$-methyl-2$\alpha$-trideuteriomethyl-6$\beta$-phthalimidopencillanate-1-oxide and 0.20 g. (1.5 mmol) N-chlorosuccinimide was refluxed for 30 min. in 25 ml. of dry, 1,1,2-trichloroethane, cooled, washed with water (1 × 50 ml), brine (1 × 50 ml), and dried (MgSO$_4$). The solvent was then evaporated in vacuo to provide 0.69 g. of a mixture of R- and S-sulfinyl chlorides as a light yellow amorphous foam. This mixture was then dissolved in 25 ml. of dry methylene chloride and 0.20 (1.7 mmol) of anhydrous stannic chloride was added. The resulting mixture was stirred for 50 min., washed with 1N. hydrochloric acid, dried (MgSO$_4$), and evaporated in vacuo yielding 0.57 g. of a mixture of R- and S-sulfoxides as a yellow foam. The material so obtained was dissolved in 4 ml. of dry N,N-dimethylformamide, cooled in an ice bath and 0.14 ml. (1.6 mmol) of phosphorus trichloride was then added. After 35 min. the crude mixture was poured onto water-cracked ice and stirred. The resulting precipitate was collected by filtration and dried under vacuum. Yield was 0.38 g. The nmr spectrum exhibited only a very small signal for the C$_2$ position (<10% of theory by nmr integration) while the signal for the exomethylene C'$_3$ position was normal indicating selective incorporation of the deuterium into the C$_2$ position. Mass spectral analysis gave the following deuterium (H$^2$) distribution in the C$_2$ position: d$_0$, 2.2%; d$_1$ 25.5%; d$_2$, 72.3% ± 2%. Recrystallization from methylene chloride/cyclohexane gave colorless crystals, mp 198°–201° (dec); mass spectrum m/e 360, 273, 174; ir (KBr) 1770, 1740, and 1710 cm$^{-1}$; nmr (CDCl$_3$) $\delta$3.80 (s, 3), 5.32 (m, 3), 5.46 (d, 1, J=4.5 Hz), 5.67 (d, 1, J=4.5 Hz), 7.83 (m, 4).

Anal. Calcd. for C$_{17}$H$_{14}$N$_2$O$_5$S (358.372): C, 56.98; H, 3.94; N, 7.82; O, 22,32; S, 8.95.

Found: C, 56.96; H, 3.85; N, 7.94.

EXAMPLE 3

4'-Nitrobenzyl 7-phenoxyacetamido-3-methylenecepham-4-carboxylate-1-oxide

A. Stannic chloride.

A mixture of 6.0 g. (12 mmol) of 4'-nitrobenzyl-6-phenoxyacetamidopenicillanate 1-oxide and 500ml. of dry toluene was refluxed for 10 minutes by using a Dean-Stark trap to remove a trace amount of water. Then 1.8 g. of N-chlorosuccinimide was added and the mixture was refluxed for 90 minutes and cooled to ca. 50°. To the resulting solution of sulfinyl chloride 1.8 ml. of anhydrous stannic chloride was added. The mixture was stirred at room temperature for 90 minutes. Then 100 ml. of water and 100 ml. of ethyl acetate was added. The organic layer was separated and washed (1N.HCl, aqueous NaHCO$_3$, brine), and dried (MgSO$_4$). Evaporation in vacuo to dryness provided a product which crystallized from ethyl acetate to give 2.16 g. (36%) of the title product. A sample was recrystallized from ethyl acetate/acetone to give large prisms (m.p.

200°-201°): nmr (CDCl₃) δ3.5 and 3.75 (ABq, 2, J=14 Hz), 4.55 (s, 2), 4.83 (d, 1, J=4.5 Hz), 5.3 (s, 2), 5.33 (s, 1), 5.5 (s, 1), 5.78 (s, 1), 5.94 and 6.1 (q, 1, J=4.5 Hz and 8.0 Hz), 6.9–8.3 (m, 9).

Anal. Calcd. for C₂₃H₂₁N₃O₈S (499.5): C, 55.31; H, 4.24; N, 8.41; O, 25.62; S, 6.42.

Found: C, 55.06; H, 4.14; N, 8.30; O, 25.62; S, 6.26.

B. Zinc chloride.

4'-Nitrobenzyl 3-methyl-2-(2-chlorosulfinyl-4-oxo-3-phenoxyacetamido-1-azetidinyl)-3-butenoate was prepared by refluxing a solution of 1 g. of 4'-nitrobenzyl 6-phenoxyacetamidopenicillanate sulfoxide and 0.27 g. of N-chlorosuccinimide in 40 ml. of 1,1,2-trichloroethane for 30 minutes. Then 0.27 g. of zinc chloride was added to the reaction mixture. The mixture was then refluxed for an additional 45 minutes. After cooling the mixture to room temperature, it was washed with 1N.HCl (2X), dried (MgSO₄), and evaporated in vacuo to dryness. An nmr spectrum of the product showed it to be the desired 4'-nitrobenzyl 7-phenoxyacetamido-3-methylenecepham-4-carboxylate 1-oxide.

C. Silver p-toluenesulfonate

A solution of 1 g. of 4'-nitrobenzyl 6-phenoxyacetamidopenicillanate 1-oxide and 0.27 g. of N-chlorosuccinimide in 10 ml. of dry toluene was refluxed for 1 hour. Silver p-toluenesulfonate (0.61 g.) was added to the hot solution. The mixture was stirred for 45 minutes (while cooling to room temperature). The reaction mixture was filtered, washed with water (2X) and brine, dried (MgSO₄), and evaporated in vacuo to dryness to provide 0.43 g. 4'-nitrobenzyl 7-phenoxyacetamido-3-methylenecepham-4-carboxylate 1-oxide (with some impurities) as a yellow foam.

EXAMPLE 4

4'-Nitrobenzyl 7-phthalimido-3-methylenecepham-4-carboxylate 1-oxide

To a solution of 23.1 g. of 4'-nitrobenzyl 3-methyl-2-(2-chlorosulfinyl-4-oxo-3-phthalimido-1-azetidinyl)-3-butenoate in 400 ml. of dichloromethane at room temperature was added 6.1 ml. of anhydrous stannic chloride. An increasing amount of precipitate was noted as the reaction progressed. After 45 minutes the reaction mixture was washed with 1N. sulfuric acid, water, sodium bicarbonate solution, and brine. The organic layer was dried and evaporated in vacuo to dryness to provide 16.72 g. (78%) of the title product. The R- and S-sulfoxide isomers were separated by fractional recrystallization from acetone and dichloromethane.

The R-sulfoxide is obtained as colorless prisms which softened at 155° and melted completely at 213°: ir (CHCl₃) 1790, 1780, 1738 and 1723 cm⁻¹; mass spectrum m/e 495, 479, 367, 343; nmr (CDCl₃) δ3.58 and 4.10 (ABq, 2, J=13 Hz), 4.87 (d, 1, J=4.5 Hz), 5.33 (s), 5.57 (m, 2), 5.95 (d, 1, J=4.5 Hz), 7.4–8.4 (m, 8, ArH).

Anal. Calcd. for C₂₃H₁₇N₃O₈S (495.5): C, 55.76; H, 3.46; N, 8.48; O, 25.83; S, 6.47.

Found: C, 55.50; H, 3.45; N, 8.65; O, 25.17; S, 6.32.

The S-sulfoxide was isolated as colorless prisms (mp 190°-192°): ir (mull) 1780, 1775, 1741 and 1728 cm⁻¹; nmr (CDCl₃) δ3.5 and 3.7 (ABq, 2, J=15 Hz), 4.9 (d, 1, J=4.5 Hz), 5.34 (s, 2), 5.46 (m, 2), 5.6 (d, 1, J=4.5 Hz). 5.8 (s, 1), 7.4–8.4 (m, 8).

Anal. Calcd. for C₂₃H₁₇N₃O₈S C, 55.76; H, 3.46; N, 8.48; O, 25.83; S, 6.47.

Found: C, 55.58; H, 3.62; N, 8.25; O, 25.19; S, 6.18.

EXAMPLE 5

2', 2', 2'-Trichloroethyl 7-phenylacetamido-3-methylenecepham-4-carboxylate 1-oxide A mixture of 1.0 g. of 2', 2', 2'-trichloroethyl 7-phenylacetamidopenicillanate 1-oxide, 0.5 g. of N-chlorosuccinimide and 80 ml. of dry toluene was refluxed for 90 minutes, then cooled, and washed (water and brine). To the resulting solution of sulfinyl chloride was added 0.28 ml. of anhydrous stannic chloride. The resulting mixture was stirred for 90 minutes. After washing (water and brine) the solvent was evaporated in vacuo to dryness. The product crystallized from ethyl acetate-ether to provide the title product as colorless prisms: m.p. 187°–189°; nmr (CDCl₃) δ3.5 and 3.81 (ABq, 2, J=14 Hz); 3.63 (s, 2), 4.8 (m, 2), 4.9 (d, 1, J=4.5 Hz), 5.37 (s, 1), 5.5 (s, 1), 5.82 (s, 1), 5.9 and 6.07 (q, 1, J=4.5 Hz and 10.0 Hz), 7.0 (d, NH, J=10 Hz), 7.33 (s, 5).

EXAMPLE 6

Methyl 7-(2,2-dimethyl-3-nitroso-5-oxo-4-phenylimidazolidin-1-yl)-3-methylenecepham-4-carboxylate 1-oxide A mixture of 0.896 g. of N-nitrosohetacillin sulfoxide methyl ester and 0.536 g. of N-chlorosuccinimide in 55 ml. of dry benzene was refluxed under nitrogen for about 1 hour. The reaction mixture was cooled and a 5 ml. aliquot of the mixture was evaporated in vacuo to dryness. The nmr spectrum of the residue thereby obtained was consistent with the structure of the desired intermediate sulfinyl chloride. The remainder of the reaction mixture was cooled under nitrogen in an ice bath, and 0.33 ml. of stannic chloride was added. A light orange precipitate formed immediately. After stirring the mixture for 2 hours and 15 minutes at room temperature, 5.5 ml. of dimethylacetamide and 55 ml. of ethyl acetate was added. The resulting solution was washed with water and brine, dried over CaSO₄, and evaporated in vacuo to dryness to provide 1.3 g. of a yellow oil. The product was dissolved in methylene chloride and applied to 4 preparative thin-layer chromatography plates. The plates were developed with a 1:1 mixture of benzene and ethyl acetate. Two primary bands were noted, the one having the lower rf value representing the title compound. The 3-methylenecepham sulfoxide (a mixture of R- and S-sulfoxides) was isolated by extracting the identified band with acetonitrile: nmr (CDCl₃) δ2.07 (s, 6, gem-dimethyl), 3.73 (s, 3, COOCH₃), 4.7–5.6 (m), and 7.3 (s, ArH).

EXAMPLE 7

4'-Nitrobenzyl 3-methyl-2-(2-sulfino-4-oxo-3-phthalimido-1-azetidinyl)-3-butenoate A solution of 49.7 g. (0.1 mol) 4'-nitrobenzyl 6-phthalimidopenicillanate 1-oxide and 13.4 g. of (0.1 mol) of N-chlorosuccinimide in 1.51 l. of 1,2-dichloroethane was refluxed for 70 minutes. After cooling the reaction mixture was washed with water and brine, dried (MgSO₄). The solvent was evaporated in vacuo to dryness to provide 52.0 g. of the azetidinone sulfinyl chloride product: nmr (CDCl₃) δ1.97 (s, 3), 5.05 (s, 1), 5.4 (s, 2), 5.76 (d, 1, J=5 Hz), 5.91 (d, 1, J=5 Hz), 7.83 (m, 8, ArH).

The sulfinyl chloride was converted to the sulfinic acid by slurrying an ethyl acetate solution thereof with a 5% solution of sodium bicarbonate at room temperature for 2 hours. Acidification of the aqueous layer with hydrochloric acid in the presence of ethyl acetate provided, after separation, drying (MgSO$_4$), and evaporation in vacuo of the organic layer, the desired sulfinic acid as a colorless foam: nmr (CDCl$_3$) δ1.92 (s, 3), 4.88 (s, 1, J=4.5 Hz), 5.00 (s, 2), 5.18 (broad s, 1), 5.38 (s, 2), 5.67 (d, 1 J=4.5 Hz), and 7.5–8.3 (m, 9, ArH).

EXAMPLE 8

2', 2', 2'-Trichloroethyl 7-phenoxyacetamido-3-methylenecepham-4-carboxylate 1-oxide A mixture of 4.82 g. (10 mmol) of 2',2',2'-trichloroethyl 6-phenoxyacetamidopenicillanate 1-oxide, 150 ml. of dry toluene, and 2.0 (11 mmol) of N-chlorophthalimide was refluxed for 60 minutes using a Dean-Stark adapter. A 5 ml. aliquot of the mixture was evaporated; the nmr spectrum thereof showed a complete conversion to the expected sulfinyl chloride.

The solution of the sulfinyl chloride in toluene was cooled to ca. 40°, and 1.4 ml. of stannic chloride was added. The mixture was stirred for 60 minutes and then was washed successively with 1N.HCl, aqueous NaHCO$_3$, and brine and dried (MgSO$_4$). After evaporation of the solvent, 30 ml. of chloroform was added to the residue, and the insoluble phthalimide was filtered. The filtrate was evaporated to dryness and the yellow amorphours product was dried in vacuo. Yield: 3.4 g. (70 percent) of the title compound; nmr (CDCl$_3$) 3.56 and 3.80 (ABq, 2, J=14 Hz), 4.48 (s, 2), 4.75 (m, 2, CH$_2$CCl$_3$), 4.89 (d, 1, J=4.5 Hz), 5.33 (s, 1), 5.48 (s, 1), 5.78 (s, 1), 5.9 and 6.07 (q, 1, J=4.5 Hz), 6.8–7.4 (m, 5, ArH), and 8.1 (d, NH, J=10 Hz).

EXAMPLE 9

Methyl 3-methyl-2-(2-sulfino-4-oxo-3-phthalimido-1-azetidinyl)-3-butenoate

A mixture of 3.76 g. of methyl 6-phthalimidopenicillinate sulfoxide and 1.4 g. of N-chlorosuccinimide in 250 ml. of dry (CaCl$_2$) carbon tetrachloride was refluxed for 70 minutes. The mixture was cooled to room temperature, filtered, washed with water and brine and dried (MgSO$_4$). Evaporation in vacuo to dryness provided methyl 3-methyl-2-(2-chlorosulfinyl-4-oxo-3-phthalimido-1-azetidinyl)-3-butenoate as a white foam (See Example 1A).

To a solution of 0.20 g. of the sulfinyl chloride in 25 ml. of chloroform was added 2 drops of water. The mixture was refluxed for 30 minutes, cooled, dried (MgSO$_4$) and evaporated in vacuo to dryness to provide the title product as a colorless foam: nmr (CDCl$_3$) δ1.93 (s, 3, —CH$_3$), 3.80 (s, 3, —COOCH$_3$), 4.88–5.15 (m, 4, C$_3$—H, =CH$_2$, β-lactam H), 5.70 (d, 1 J=5.0 Hz, β-lactam H), 7.80 (m, 4, ArH). The sulfinyl chloride is also converted to the title sulfinic acid upon standing at room temperature open to the air for 2 days.

EXAMPLE 10

Methyl 7-phthalimido-3-methylenecepham-4-carboxylate 1-oxide (from azetidinone sulfinic acid)

A. Phosphorous Pentoxide.

A solution of 0.10 g. of methyl 3-methyl-2-(2-sulfino-4-oxo-3-phthalimido-1-azetidinyl)-3-butenoate and 0.04 g. of phosphorous pentoxide in 20 ml. of 1,2-dichloroethane was stirred at room temperature for 1 hour. A tlc of the reaction mixture indicated only trace amounts of the methylenecepham sulfoxide. The mixture was then refluxed for 30 minutes, cooled to room temperature, and combined with 25 ml. of ethyl acetate and 50 ml. of brine. The organic layer was separated, washed with aqueous sodium bicarbonate and brine and dried (MgSO$_4$). Evaporation in vacuo to dryness provided 0.04 g. of the title product as a white froth.

B. Sulfuric acid.

The same procedure was followed as that described in Example 1 (J) above except 0.20 g. of methyl 3-methyl-2-(2-sulfino-4-oxo-3-phthalimido-1-azetidinyl)-3-butenoate was employed as the starting material instead of the sulfinyl chloride. The procedure provided 0.03 g. of the title compound.

C. Polyphosphoric acid.

The same procedure was followed as in Example 1 (I) above except 0.20 g. of methyl 3-methyl-2-(2-sulfino-4-oxo-3-phthalimido-1-azetidinyl)-3-butenoate was employed as the starting material instead of the sulfinyl chloride. The reaction provided 0.10 g. of the title compound.

D. Trifluoroacetic acid.

The same procedure was followed as described in Example 1 (L) above except 0.20 g. of methyl 3-methyl-2-(2-sulfino-4-oxo-3-phthalimido-1-azetidinyl)-3-butenoate was employed as the starting material instead of the corresponding sulfinyl chloride. An nmr spectrum of the product showed the title compound to be the major constituent.

EXAMPLE 11

4'-Nitrobenzyl 3-methyl-2-[2-chlorosulfinyl-4-oxo-3-(N-phenoxyacetyl-N-(2,2,2-trichloroethoxycarbonyl)amino)-1-azetidinyl]-3-butendate A. A mixture of 4.855 g. (10 mmol) of 4'-nitrobenzyl 6-phenoxyacetamido-2,2-dimethylpenam-3-carboxylate, 16.94 g. (80 mmol) of 2,2,2-trichloroethyl chloroformate, 18 ml. of N,O-(bis-trimethylsilyl)trifluoromethylacetamide, and 20 ml. of methylene chloride was prepared. The mixture was permitted to stand at room temperature overnight. The mixture then was heated at reflux for 7 hours after which it was again permitted to stand at room temperature overnight. Heating then was continued for an additional 6 hours. The mixture then was evaporated to a residue; the residue was dissolved in benzene, and the resulting solution then was added to a large excess of heptane. The resulting insoluble material was filtered off, dissolved in benzene, and chromatographed over silica gel using a benzene-ethyl acetate elution gradient. 4'-Nitrobenzyl 6-[N-phenoxyacetyl-N-( 2,2,2-trichloroethoxycarbonyl)amino]-2,2-dimethylpenam-3-carboxylate (4.76 g.; 72 percent) was obtained as product: nmr (CDCl$_3$) δ1.41 (s, 3), 1.62 (s, 3), 4.61 (s, 1), 4.84 (d, 1, J=12 Hz), 4.99 (d, 1, J=12 Hz), 5.20 (s, 2), 5.30 (s, 2), 5.56 (s, 2), 6.8–7.4 (m, 5), 7.53 (d, 2, J=9 Hz), and 8.22 (d, 2, J=9 Hz).

B. Sulfoxide preparation.

To about 75 ml. of acetone were added 2.54 g. (3.84 mmol) of the above product. The mixture was cooled to −70° C., and an excess of ozone was admitted to the reaction mixture at approximately 1.17 mmol per minute for nine minutes during which time the reaction mixture turned blue. The mixture was maintained at −70° C. for about 35 minutes after which it was warmed to room temperature. The solvent was removed in vacuo to obtain 2.76 g. of 4'-nitrobenzyl 6-[N-phenoxyacetyl-N-(2,2,2-trichloroethoxycarbonyl)amino]-2,2-dimethylpenam-3-carboxylate-1-oxide. nmr (CDCl$_3$) δ1.22 (s, 3), 162 (s, 3), 4.60 (s, 1), 4.78 (d, 1, J=5Hz), 4.93 (s, 2), 5.26 (s, 2), 5.30 (s, 2), 5.93 (d, 1, J=5Hz), 6.8–7.4 (m, 5), 7.51 (d, 2, J=9 Hz) and 8.20 (d, 2, J=9 Hz).

C. Sulfinyl chloride preparation.

To 40 ml. of dry benzene were added 792 mg. (about one mmol) of the above product and 155 mg. (about 1.2 mmol) of N-chlorosuccinimide. The resulting mixture was heated at reflux for one hour. An nmr of the reaction mixture indicated the presence of the title compound: nmr (CDCl$_3$) δ1.92 (s, 3), 4.89 (s, 1), 4.96 (s, 2), 5.05 (s, 2), 5.23 (s, 2), 5.26 (s, 1), 5.34 (s, 2), 5.64 (d, 1, J=5 Hz), 5.95 (d, 1, J=5 Hz), 6.10 (d, 1, J=5 Hz), 6.8–7.5 (m, 5), 7.56 (d, 2, J=9 Hz), and 8.23 (d, 2, J=9 Hz).

D. Conversion to 4'-Nitrobenzyl 7-[N-phenoxyacetyl-N-(2,2,2-trichloroethoxycarbonyl)amino]-3-methylenecepham-4-carboxylate-1-oxide To the reaction mixture from (C) above, cooled to room temperature, were added 390 mg. (1.5 mmol) of stannic chloride. The mixture was maintained at room temperature for 75 minutes, and 5 ml. of methanol then were added. Additional benzene was added, and the resulting mixture was washed three times with a mixture of HCl and aqueous sodium chloride. The benzene layer was separated, dried over sodium fulfate, and evaporated in vacuo to dryness. The residue was chromatographed over silica gel (15% water) with a benzene-ethyl acetate gradient to obtain 246 mg. of the exomethylenecepham sulfoxide: nmr (CDCl$_3$) δ3.42 (d, 1, J=13 Hz), 3.98 (d, 1, J=13 Hz), 4.64 (d, 1, J=5 Hz), 4.94 (s, 2), 5.25 (s, 2), 5.30 (s, 2), 5.34 (s, 1), 5.47 (s, 1), 6.04 (d, 1, J=5 Hz), 6.8–7.4 (m, 5), 7.55 (d, 2, J=9 Hz), and 8.23 (d, 2, J=9 Hz).

EXAMPLE 12

4'-Bromophenacyl 7-Phenoxyacetamido-3-methylenecepham-4-carboxylate-1-oxide

To 200 ml. of dried toluene were added 5.6 (10 mmol) of 4'-bromophenacyl 6-phenoxyacetamido-2,2-dimethylpenam-3-carboxylate-1-oxide and 5.2 g. (50 mmol) of sodium bisulfite. The mixture was heated at reflux, and 1.5 g. (11 mmol) of N-chlorosuccinimide were added. The resulting mixture was stirred and refluxed for one hour, cooled in an ice bath, and 1.3 g. (11 mmol) of stannic chloride then were added. The resulting mixture was stirred at room temperature for about two hours and then was poured into a mixture of ethyl acetate and water. The organic layer was separated and washed successively with 5 percent hydrochloric acid, 5 percent sodium bicarbonate solution, and brine. The mixture then was dried over magnesium sulfate. Upon evaporation to near dryness in vacuo, 1.75 g. (31 percent) of the title compound crystallized and was collected. An nmr analysis of the product was consistent with the structure of the title compound.

Anal. Calcd. for $C_{24}H_{21}N_2O_7SBr$: C, 51,35; H, 3.77; N, 4.99; Br, 14.23. Found: C, 51.03; H, 3.91; N, 5.10; Br, 14.46.

EXAMPLE 13

7-Phenoxyacetamido-3-Methylenecepham-4-carboxylic acid-1-oxide

To 200 ml. of dried toluene were added 4.95 g. (10 mmol) of 4'-methoxybenzyl 6-phenoxyacetamido-2,2-dimethylpenam-3-carboxylate-1-oxide and 5.2 g. (50 mmol) of sodium bisulfite. The mixture was heated at reflux, and 1.5 g. (11 mmol) of N-chlorosuccinimide were added. The mixture then was stirred and refluxed for one hour after which it was cooled in an ice bath, and 1.3 gms. (11 mmol) of stannic chloride were added. The mixture then was stirred at room temperature for about 2 hours after which it was poured into a mixture of ethyl acetate and water. The organic layer was separated and washed successively with 5 percent hydrochloric acid and brine. The organic layer then was extracted with 5 percent sodium bicarbonate solution. The extract was slurried with ethyl acetate, and acidified to pH 2.5. The ethyl acetate layer was separated, washed with water, dried over magnesium sulfate, and concentrated in vacuo to a small volume from which 1.3 gms. (35 percent) of the title compound were obtained as crystals. Analysis of the product by nmr was consistent with the structure of the title compound.

Anal. Calcd. for $C_{16}H_{16}N_2O_6S$: C, 52.74; H, 4.43; N, 7.69. Found: C, 52.99; H, 4.64; N, 7.51.

EXAMPLE 14

Benzhydryl 3-methyl-2-(2-chlorosulfinyl-4-oxo-3-phenoxyacetamido-1-azetidinyl)-3-butenoate A. To 800 ml. of dried toluene were added 20 g. of benzhydryl 6-phenoxyacetamido-2,2-dimethylpenam-3-carboxylate-1-oxide. The mixture was refluxed in a system having a Dean-Stark water trap to azeotropically remove any moisture. To the mixture then were added 12.2 g. of N-chlorosuccinimide. Refluxing was continued for 1.5 hours. The product was analyzed by nmr analysis which was consistent with the structure of the title compound: nmr (CDCl$_3$) δ1.88 (s, 3), 4.53 (s, 2), 4.90 (s, 1), 5.14 (s, 2), 5.54 (d, 1, J=4 Hz), 6.24 (q, 1, J=4Hz and 8 Hz), 6.95 (s, 1), 7.15–7.4 (m, 15), and 8.0 (d, 1, J=8 Hz).

B. Conversion to exomethylene sulfoxide.

In accordance with the procedure described in Example 13 hereinabove, the azetidinone sulfinyl chloride from (A) was cyclized with stannic chloride to 7-phenoxyacetamido-3-methylenecepham-4-carboxylic acid-1-oxide.

EXAMPLE 15

2',2',2'-Trichloroethyl 3-methyl-2-[2-chlorosulfinyl-4-oxo-3-(4-nitrobenzyloxycarbamido)-1-azetidinyl]-3-butenoate A. A mixture of 300 ml. of 1,1,2-trichloroethane and 10.26 g. of 2', 2',2'-trichloroethyl 6-(4-nitrobenzyloxycarbamido)-2,2-dimethylpenam-3-carboxylate-1-oxide was prepared. The mixture was refluxed with removal of about 75 ml. of the solvent to promote drying of the reaction medium. The mixture then was cooled, and propylene oxide was added followed by 4 g. of N-chlorosuccinimide. The temperature of the mixture was raised to 102° C., and the mixture was refluxed for 2.5 hours. A sample of the reaction mixture was removed; the solvent was evaporated. An nmr analysis of the residue was consistent with the structure of the title compound: nmr (CDCl₃) δ1.94 (bs, 3), 4.83 (s, 2), 5.25 (s, 2), 5.0–5.4 (m, 3), 6.2 (d, 1, J=4Hz), 7.55 (d, 2, J=8 Hz), and 8.24 (d, 2, J=8 Hz).

B. Conversion to 2',2',2'-trichloroethyl 7-(4-nitrobenzyloxycarbamido)-3-methylenecepham-4-carboxylate-1-oxide.

A portion representing about one-third of the reaction mixture from (A) above was evaporated, and the residue was dissolved in 100 ml. of dried methylene chloride. To the resulting mixture were added 5 ml. of stannic chloride. The mixture was treated in accordance with the method of Example 12 to obtain 700 mg. of the 3-methylenecepham sulfoxide: nmr (CDCl₃) δ3.60, 3.88 (ABq, 2, J=15 Hz), 4.82 (s, 2), 4.94 (d, 1, J=4.5 Hz), 5.23 (s, 2), 5.40 (s, 1), 5.56 (s, 1), 5.83 (s, 1), 6.37 (d, 1, J=10 Hz), 7.46 (d, 2, J=9 Hz), and 8.20 (d, 2, J=9 Hz).

EXAMPLE 16

4'-Nitrobenzyl 3-methyl-2-(2-chlorosulfinyl-4-oxo-3-acetamido-1-azetidinyl)-3-butenoate A. Toluene (500 ml.) was heated in equipment having a Dean-Stark water trap to azeotropically remove any moisture. To the resulting dried toluene was added 1.0 g. (2.4 mmol) of 4'-nitrobenzyl 6-acetamido-2,2-dimethylpenam-3-carboxylate-1-oxide. The resulting mixture was refluxed again using a Dean-Stark water trap to remove any additional amounts of water. The mixture then was cooled, and 400 mg. (2.9 mmol) of N-chlorosuccinimide were added. The mixture then was refluxed for 1 hour. A sample of the reaction mixture was withdrawn, and the solvent was removed. The product which was obtained was consistent by nmr analysis with the structure of the title compound: nmr (CDCl₃) δ1.86 (bs, 3), 2.04, 2.09 (2s, 3), 4.80 (m, 1), 5.2 (m, 2), 5.28 (s, 2), 5.63 (m, 1), 6.05 (d, 1, J=4 Hz), and 7.4–8.4 (q, 4, ArH).

B. Conversion to 4'-Nitrobenzyl 7-acetamido-3-methylenecepham-4-carboxylate-1-oxide The reaction mixture from (A) above was cooled to an ice bath, and 1 ml. of stannic chloride was added. The mixture was maintained for two hours at room temperature after which it was evaporated in vacuo to dryness. The resulting residue was dissolved in ethyl acetate, and the ethyl acetate mixture was washed once with a mixture of HCl and aqueous sodium chloride and twice with aqueous sodium chloride, dried over magnesium sulfate, and evaporated in vacuo to dryness. The residue was dissolved in a minimum of ethyl acetate, and, after standing overnight, crystals of the 3-methylenecepham sulfoxide formed and were collected: nmr (CDCl₃) δ1.92 (s, 3), 3.80 (bs, 2), 5.00 (d, 1, J=4 Hz), 5.32 (s, 2), 5.45–5.80 (m, 5), 7.60 (d, 2, J=8 Hz), 7.86 (d, 1, J=9 Hz), and 8.20 (d, 2, J=8 Hz).

EXAMPLE 17

4'-Nitrobenzyl 7-phenoxyacetamido-3-methylenecepham-4-carboxylate-1-oxide. (Complex isolation)

Toluene (750 ml.) was refluxed for 15 minutes using a Dean-Stark trap. To the dried toluene were added 35 ml. of propylene oxide, 25 g. of 4'-nitrobenzyl 6-phenoxyacetamidopenicillanate-1-oxide and 7.37 g. of N-chlorosuccinimide. The reaction mixture was refluxed at 100° C. for 2 hours after which time 120 ml. of toluene was distilled from the mixture. After cooling, 7.3 ml. of stannic chloride was added. Filtration of the reaction mixture provided 17.1 g. f an orange complex which was dissolved in ethyl acetate and washed with aqueous HCl and brine. The ethyl acetate solution was dried and evaporated in vacuo to dryness to provide 6.9 g. of the title product.

EXAMPLE 18

Methyl 3-methyl-2-(2-bromosulfinyl-4-oxo-3-phthalimido-1-azetidinyl)-3-butenoate A. A mixture of 1.88 g. of methyl 6-phthalimidopenicillanate-1-oxide and 890 mg. of N-bromosuccinimide in 150 ml. of carbon tetrachloride was refluxed for 80 minutes. The reaction mixture was cooled, washed with water and brine, dried over anhydrous MgSO₄, and evaporated in vacuo to dryness to provide 1.82 g. of the title product: nmr (CDCl₃) δ1.98 (bs, 3), 3.82 (s, 3, COOC$\underline{H}$₃), 5.0–5.35 (m, 3), 5.8–6.2 (m, 2, β-lactam H), and 7.80 (bs, 4, ArH).

B. Conversion to exomethylenecepham sulfoxide.

The azetidinone sulfinyl bromide from above was dissolved in 20 ml. of methylene chloride; 0.6 ml. of stannic chloride was added to the solution. After 45 minutes at room temperature the reaction mixture was washed with water and brine, dried over anhydrous MgSO₄, and evaporated in vacuo to dryness to provide 1.15 g. of methyl 7-phthalimido-3-methylenecepham-4-carboxylate-1-oxide (a mixture of R- and S-sulfoxide isomers). For the predominant isomer: nmr (CDCl₃) δ3.64, 4.20 (ABq, 2, J=13.0 Hz, C₂—H), 3.84 (s, 3, COOC$\underline{H}$₃), 4.90 (d, 1, J=4.0 Hz, β-lactam H), 5.3–5.7 (m, 3), 5.97 (d, 1, J=4.0 Hz, β-lactam H), and 7.84 (bs, 4, ArH).

EXAMPLE 19

4'-Nitrobenzyl 3-methyl-2-(2-isopropylthiosulfinyl-4-oxo-3-phenoxyacetamido-1-azetidinyl)-3-butenoate A. To a solution of 10 g. of 4'-nitrobenzyl 3-methyl-2-(2-chlorosulfinyl-4-oxo-3-phenoxyacetamido-1-azetidinyl)-3-butenoate in 450 ml. of toluene was added 1.9 ml. of isopropyl mercaptan and 3.5 ml. of propylene oxide. The mixture was allowed to stand for several days at room temperature and then was evaporated in vacuo to dryness to provide an oil which was chromatographed on a silica gel column using a toluene-ethylacetate gradient. A total of 6.62 g. of the title product was isolated: nmr (CDCl₃) δ1.40 (d, 6, J=6.0 Hz, SCH(C$\underline{H}$₃)₂), 2.01 (s, 3), 3.55 (m, 1, SC$\underline{H}$(CH₃)₂), 4.60 (s, 2, side chain CH₂), 5.1–5.4 (m, 3), 5.33 (s, 2, ester CH₂), 6.20 (dd, 1, J=4.5 and 10.0 Hz, β-lactam H), 6.9–8.3 (m, 9, ArH) and 8.6 (d, 2, J=10.0 Hz, N$\underline{H}$).

B. Conversion to exomethylenecepham sulfoxide.

The title product (682 mg.) was dissolved in 3.4 ml. of methane sulfonic acid. After 30 minutes the solution was poured into a separatory funnel containing ethyl acetate and saturated aqueous sodium bicarbonate solution. The organic layer was separated, washed successively with aqueous sodium bicarbonate, water and brine (2X), and dried over anhydrous MgSO₄. The product crystallized from ethyl acetate upon standing overnight. A total of 60 mg. of 4'-nitrobenzyl 7-phenoxyacetamido-3-methylenecepham-4-carboxylate-1-oxide was isolated.

EXAMPLE 20

4'-Nitrobenzyl 3-methyl-2-(2-tert-butylthiosulfinyl-4-oxo-3-phenoxyacetamido-1-azetidinyl)-3-butenoate A. The same procedure was followed as described in Example 19 except 2.4 ml. of tert-butyl mercaptan was used in place of isopropyl mercaptan. 4.69 g. of the title product was isolated after chromatography: nmr (CDCl$_3$) $\delta$1.43 (s, 9, tert-butyl), 2.01 (s, 3), 4.57 (s, 2, side chain —CH$_2$), 5.0–5.4 (m, 5), 6.20 (dd, 1, J=4.0 and 11.0 Hz, $\beta$-lactam H), 6.8–8.2 (m, 9, ArH) and 8.64 (d, 1, J=11.0 Hz, N$\underline{H}$).

B. Conversion to exomethylenecepham sulfoxide.

The title product (700 mg.) was dissolved in 3.5 ml. of methanesulfonic acid. Following the same procedures as described in the second paragraph of Example 19, 190 mg. of 4'-nitrobenzyl 7-phenoxyacetamido-3-methylenecepham-4-carboxylate-1-oxide was isolated.

EXAMPLE 21

4'-Nitrobenzyl 3-methyl2-(2-methoxysulfinyl-4-oxo-3-phenoxyacetamido-1-azetidinyl)-3-butenoate A. To a solution of 4'-nitrobenzyl 3-methyl-2-(2-chlorosulfinyl-4-oxo-3-phenoxyacetamido-1-azetidinyl)-3-butenoate, derived from 10 g. of 4'-nitrobenzyl 6-phenoxyacetamidopenicillanate-1-oxide and 2.68 g. of N-chlorosuccinimide, in 400 ml. of toluene was added 25 ml. of dry methanol. The reaction mixture was stirred at room temperature overnight, and then was washed successively with aqueous sodium bicarbonate (2X), water, and brine (2X). Evaporation in vacuo to dryness yielded 10 g. of the impure title product which was purified by chromatography over acid-washed silica gel using a toluene-ethyl acetate gradient. The product was isolated as a mixture of isomers (R- and S-sulfinates). For the predominant isomer: nmr (CDCl$_3$) $\delta$1.90 (s, 3), 3.74 (s, 3, —OCH$_3$), 4.52 (s, 2, side chain CH$_2$), 4.8–5.3 (m, 5), 5.32 (s, 2, ester CH$_2$), 5.76 (dd, 1, J=5.0 and 9.0 Hz, $\beta$-lactam H), and 6.8–8.2 (m, 9, ArH).

B. Conversion to exomethylenecepham sulfoxide.

The title product (590 mg.) was dissolved in 2.0 ml. of methanesulfonic acid. After 30 minutes at room temperature, the mixture was worked-up in accordance with the procedures described in the second paragraph of Example 19 hereinabove to provide 0.13 g. (40%) of 4'-nitrobenzyl 7-phenoxyacetamido-3-methylenecepham-4-carboxylate-1-oxide.

EXAMPLE 22

4'-Nitrobenzyl 3-methyl-2-(2-menthyloxysulfinyl-4-oxo-3-phenoxyacetamido-1-azetidinyl)-3-butenoate A. The same procedure was followed as described in Example 21 except 3.12 g. (20 mmol) of menthol was employed instead of methanol. The product sulfinate ester was isolated by chromatography on an acid-washed silica gel column using a toluene-ethyl acetate gradient. The product was isolated as a mixture of isomers (R- and S-sulfinates). For the predominant isomer: nmr (CDCl$_3$) $\delta$0.6–2.4 (m, 18, menthyl H), 1.86 (s, 3), 3.98 (bs, 1), 4.52 (s, 2, side chain CH$_2$), 4.72 (d, 1, J=5.0 Hz, $\beta$-lactam H), 4.8–5.2 (m, 3), 5.36 (s, 2, ester CH$_2$), 5.72 (dd, 1, J=5.0 and 9.0 Hz, $\beta$-lactam H), 6.8–8.2 (m, 9, ArH), and 7.85 (d, 1, J=9.0 Hz, —N$\underline{H}$).

B. Conversion to exomethylenecepham sulfoxide.

The title product (906 mg.) was dissolved in 4.6 ml. of methanesulfonic acid. After 30 minutes at room temperature, the reaction mixture was worked-up in accordance with the procedure described in the second paragraph of Example 19 hereinabove. Conversion to 4'-nitrobenzyl 7-phenoxyacetamido-3-methylenecepham-4-carboxylate-1-oxide was confirmed by comparative thin-layer chromatography and nmr spectroscopy.

EXAMPLE 23

4'-Nitrobenzyl 3-methyl-2-(2-anilinosulfinyl-4-oxo-3-phenoxyacetamido-1-azetidinyl)-3-butenoate A. To a solution of 4'-nitrobenzyl 3-methyl-2-(2-chlorosulfinyl-4-oxo-3-phenoxyacetamido-1-azetidinyl)-3-butenoate, derived from 10 g. of 4'-nitrobenzyl 6-phenoxyacetamidopenicillanate-1-oxide and 2.68 g. of N-chlorosuccinimide, in 400 ml. of toluene were added 3.6 ml. of aniline. After 5 minutes at room temperature the reaction mixture was washed with water (2X) and brine, dried over anhydrous MgSO$_4$, and evaporated in vacuo to dryness to provide the title product: nmr (CDCl$_3$) $\delta$1.96 (s, 3), 4.5 (s, 2, side chain CH$_2$), 5.34 (s, 2, ester CH$_2$), 5.0–5.3 (m, 3), 5.77 (dd, 1, J=4.5 and 10.0 Hz, $\beta$-lactam H), and 6.8–8.4 (m, 14, ArH).

B. Conversion to exomethylenecepham sulfoxide.

The title product (2.07 g.) was dissolved in 10 ml. of methanesulfonic acid. After 30 minutes, the solution was poured slowly into a cold mixture of saturated aqueous sodium bicarbonate and ethyl acetate. The ethyl acetate layer was separated, washed successively with aqueous sodium bicarbonate (2X), water (2X), and brine (2X), dried over anhydrous MgSO$_4$ and evaporated in vacuo to dryness. 4'-Nitrobenzyl 7-phenoxyacetamido-3-methylenecepham-4-carboxylate-1-oxide (373 mg., 21%) crystallized from an ethyl acetate solution of the impure product.

EXAMPLE 24

Methyl 3-methyl-2-(2-N-succinimidosulfinyl-4-oxo-3-phenylacetamido-1-azetidinyl)-3-butenoate A. A solution of 2.55 g. (7 mmol) of 4'-nitrobenzyl 6-phenylacetamidopenicillanate-1-oxide, 5.6 ml. (34 mmol) of N-trimethylsilylsuccinimide and 0.18 ml. of acetic acid in 41 ml. of dimethylacetamide was stirred for 3.5 hours at 105° C. After cooling, the reaction mixture was poured into a cold mixture of 50 ml. of ethyl acetate and 150 ml. of water. The water layer was extracted twice with ethyl acetate. The ethyl acetate extracts were combined, washed with water, dried over anhydrous MgSO$_4$, and evaporated in vacuo to dryness to provide 3.3 g. of methyl 3-methyl-2-(2-N-succinimidothio-4-oxo-3-phenylacetamido-1-azetidinyl)-3-butenoate: nmr (CDCl$_3$) $\delta$1.84 (s, 3), 2.78 (s, 4, succinimido), 3.65 (s, 2, side chain CH$_2$), 3.74 (s, 3, COOCH$_3$), 4.66 (s, 1), 5.0–5.5 (m, 4, $\gamma$-lactam H + olefinic CH$_2$), 7.26 (s, 5, ArH), and 7.58 (d, 1, J=8.0 Hz, —N$\underline{H}$).

The sulfenimide from above was dissolved in 50 ml. of methylene chloride at 0° C. and oxidized with 1.48 g. of m-chloroperbenzoic acid. After 1 hour at 0° C. the reaction mixture was washed successively with saturated aqueous sodium bicarbonate, water, and brine, dried over anhydrous MgSO₄ and evaporated in vacuo to dryness to provide the title product: nmr (CDCl₃) δ1.86 (s, 3), 2.60 (s, 4, succinimido H), 3.54 (s, 2, side chain CH₂), 3.78 (s, 3, COOCH₃), 4.8–5.2 (m, 3), 5.6–5.9 (m, 1, β-lactam H), 6.04 (d, 1, J=5.0 Hz, β-lactam H), and 7.3 (s, 5, ArH).

B. Conversion to exomethylenecepham sulfoxide.

The title product (469 mg., 1 mmol) was dissolved in 2.3 ml. of methanesulfonic acid. After 30 minutes at room temperature the solution was poured slowly into a mixture of saturated aqueous sodium bicarbonate and ethyl acetate. The ethyl acetate layer was separated, washed successively with aqueous sodium bicarbonate, water and brine, dried over anhydrous MgSO₄, and evaporated in vacuo to dryness. Conversion to methyl 7-phenylacetamido-3-methylenecepham-4-carboxylate-1-oxide was confirmed by comparative thin-layer chromatography and nmr spectroscopy.

EXAMPLE 25

4'-Nitrobenzyl 3-methyl-2-[2-N,N'-dicarboethoxyhydrazosulfinyl)-4-oxo-3-phenoxyacetamido-1-azetidinyl]-3-butenoate A. A solution of 10 g. of 4'-nitrobenzyl 6-phenoxyacetamidopenicillanate-1-oxide in 300 ml. of dry 1,1,2-trichloroethane was refluxed and dried using a Dean-Stark trap. After about 50 ml. of the solvent was distilled, the mixture was cooled and 6 ml. of diethylazodicarboxylate was added. The reaction mixture was refluxed for 45 minutes and thereafter was evaporated in vacuo to dryness. The residue was triturated with hexane to remove excess diethylazodicarboxylate. Further drying provided the title product as an impure yellow gum which was not further purified before conversion to the exomethylenecepham sulfoxide: nmr (CDCl₃) δ1.40 (t, 3, J=7 Hz, CH₂CH₃), 1.95 (bs, 3), 3.8–4.7 (m, 6), 5.0–5.6 (m, 5) and 6.7–8.4 (m, 9, ArH).

B. Conversion to exomethylene sulfoxide.

One gram of the product from (A) above was dissolved in 20 ml. of methanesulfonic acid. The mixture was stirred at room temperature for 20 minutes and then poured into aqueous sodium chloride solution. The aqueous solution was then extracted with 200 ml. of ethyl acetate. The ethyl acetate extract was washed with aqueous sodium bicarbonate, dried (MgSO₄) and evaporated in vacuo to dryness. The residue was purified by preparative thin layer chromatography using silica gel plates developed with 90% ethyl acetate-benzene. A total of 160 mg. of 4'-nitrobenzyl 7-phenoxyacetamido-3-methylenecepham-4-carboxylate-1-oxide was isolated.

EXAMPLE 26

4'-Nitrobenzyl 3-methyl-2-[2-(N,N'-dicarbo-tert-butoxyhydrazosulfinyl)-4-oxo-3-acetamido-1-azetidinyl]-3-butenoate A. In accordance with the procedures described in Example 25 820 mg. of 4'-nitrobenzyl 6-acetamidopenicillanate-1-oxide was reacted with 465 mg. of di-tert-butyl azodicarboxylate to provide the title product: nmr (CDCl₃) δ1.50 (s, 18, tert-butyl) 1.90 (bs, 3), 2.00

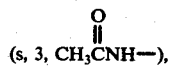
(s, 3, CH₃CNH—), 5.40 (s, 2, ester CH₂), 5.0–6.0 (m, 5) and 7.6–8.4 (m, 4, ArH).

B. Conversion to exomethylene sulfoxide.

The title product from (A) was dissolved in 15 ml. of methanesulfonic acid and after 10 minutes at room temperature was poured into saturated aqueous sodium chloride solution. The aqueous solution was extracted with ethyl acetate. The organic extract was washed with aqueous sodium bicarbonate, dried (MgSO₄), and evaporated in vacuo to dryness. Chromatographic purification of the residue provided 90 mg. (12%) of 4'-nitrobenzyl 7-acetamido-3-methylenecepham-4-carboxylate-1-oxide: nmr (CDCl₃) δ2.04

(s, 3, CH₃CNH—), 3.66 (bs, 2, C₂—H), 4.90 (d, 1, J=4.0 Hz, C₆—H), 5.26 (s, 3, C₄—H + ester CH₂), 5.45, 5.74 (2s, 2,=CH₂), 5.92 (dd, 1, J=4.0 and 8.0 Hz, C₇—H), 6.97 (d, 1, J=8.0 Hz, —NH), and 7.4–8.4 (m, 4, ArH).

EXAMPLE 27

2',2',2'-Trichloroethyl 7-(2-thienylacetamido)-3-methylenecepham-4-carboxylate sulfoxide A solution of 1 g. of 2',2',2'-trichloroethyl 6-(2-thienylacetamido)penicillanate-1-oxide and 525 mg. of di-tert-butyl azodicarboxylate in 50 ml of 1,1,2-trichloroethane was refluxed for 45 minutes. The reaction mixture was then cooled and evaporated in vacuo to dryness. The residue thereby obtained was dissolved in methanesulfonic acid and after 15 minutes at room temperature the acid solution was poured into saturated aqueous sodium chloride. The aqueous solution was extracted with ethyl acetate. The organic extract was washed with sodium bicarbonate solution, dried (MgSO₄) and evaporated in vacuo to dryness to provide 72 mg. (7%) of the title product: nmr (CDCl₃) β2.87 (bs, 2, C₂—H), 3.75 (s, 2, side chain CH₂), 4.80 (s, 2, ester CH₂), 5.28 (d, 1, J=4.0 Hz, C₆—H), 5.46, 5.77 (2s, 2,=CH₂), 5.90 (dd, 1, J=4.0 and 8.0 Hz, C₇—H) and 6.8–7.3 (m, 3, ArH).

EXAMPLE 28

4'-Nitrobenzyl 3-methyl-2-[2-(N,N'-dibenzoylhydrazosulfinyl)-4-oxo-3-phenoxyacetamido-1-azetidinyl]-3-butenoate A. In accordance with the procedures described in Example 25 10 g. of 4'-nitrobenzyl 6-phenoxyacetamidopenicillanate-1-oxide was reacted with 7.8 g. of dibenzoyldiimide in dry 1,1,2-trichloroethane.

B. Conversion to exomethylene sulfoxide.

One gram of the unpurified product from (A) above was dissolved in 20 ml. of methanesulfonic acid. After 20 minutes the mixture was poured into 300 ml. of saturated aqueous sodium chloride. The aqueous solution was extracted with 200 ml. of ethyl acetate, and the organic extract was washed with sodium bicarbonate solution, dried (MgSO₄), and evaporated in vacuo to dryness. 4'-Nitrobenzyl 7-phenoxyacetamido-3-methylenecepham-4-carboxylate-1-oxide (90 mg., 40%) was isolated by preparative thin-layer chromatography.

EXAMPLE 29

4'-Nitrobenzyl 3-methyl-2-(2-acetylhydrazosulfinyl-4-oxo-3-phenoxyacetamido-1-azetidinyl)-3-butenoate A. To a solution of 4'-nitrobenzyl 3-methyl-2-(2-chlorosulfinyl-4-oxo-3-phenoxyacetamido-1-azetidinyl)-3-butenoate (derived from 50 g. of 4'-nitrobenzyl 6-phenoxyacetamidopenicillanate-1-oxide and 15 g. N-chlorosuccinimide in 1000 ml. of 1,1,2-trichloroethane) at room temperature was added 14.8 g. of acetyl hydrazide. After stirring about 30 minutes at room temperature the reaction mixture was washed 3 times with 500 ml. portions of saturated sodium chloride solution, dried (MgSO₄) and evaporated in vacuo to dryness. The residue was dissolved in ethyl acetate. Upon standing in the refrigerator 29.7 g. (52%) of the title product crystallized: nmr (CDCl₃) δ1.94

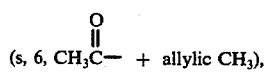
(s, 6, CH₃C— + allylic CH₃), 4.65 (s, 2, side chain CH₂), 4.9–5.4 (m, 5), 5.55 (s, 2, ester CH₂) and 6.8–8.4 (m, 9, ArH).

B. Conversion to exomethylene sulfoxide.

Two grams of the title product were dissolved in 20 ml. of methanesulfonic acid. After 15 minutes at room temperature the acid solution was poured into a separatory funnel containing 200 ml. of ethyl acetate, 250 ml. saturated sodium chloride and 250 ml. of saturated sodium bicarbonate solution. The organic layer was separated, washed with sodium bicarbonate solution, dried (MgSO₄), and evaporated in vacuo to dryness. The residue was dissolved in a minimum amount of ethyl acetate, and upon standing 879 mg. (51%) of 4'-nitrobenzyl 7-phenoxyacetamido-3-methylenecepham-4-carboxylate-1-oxide crystallized.

EXAMPLE 30

4'-Nitrobenzyl 3-methyl-2-(2-carbomethoxyhydrazosulfinyl-4-oxo-3-phenoxyacetamido-1-azetidinyl)-3-butenoate A. In accordance with the procedures described in Example 29 carbomethoxyhydrazide (4.5 g.) was reacted with the sulfinyl chloride derived from 15 g. of 4'-nitrobenzyl 6-phenoxyacetamidopenicillanate-1-oxide to provide the title product as a yellow gum: nmr (CDCl₃) δ1.92 (bs, 3), 3.66 (s, 3, COOCH₃), 4.56 (s, 2, side chain CH₂), 4.8–5.6 (m, 7, ester CH₂, β-lactam H, olefinic H) and 6.7–8.4 (m, 9, ArH).

B. Conversion to exomethylene sulfoxide.

In accordance with the procedure described in the second paragraph of Example 29, the title product (640 mg.) was cyclized in methanesulfonic acid (10 ml.) to provide 240 mg. (45%) of 4'-nitrobenzyl-7-phenoxyacetamido-3-methylenecepham-4-carboxylate-1-oxide.

EXAMPLE 31

4'-Nitrobenzyl 3-methyl-2-(2-tolylsulfonylhydrazosulfinyl-4-oxo-3-phenoxyacetamido-1-azetidinyl)-3-butenoate A. In accordance with the general procedure described in Example 29, tosyl hydrazide (18 g.) was reacted with the sulfinyl chloride derived from 30 g. of 4'-nitrobenzyl 6-phenoxyacetamidopenicillanate-1-oxide to provide the title product as a yellow gum which did not crystallize.

B. In accordance with the procedure described in the second paragraph of Example 29, the title product was cyclized in methanesulfonic acid (150 ml.) to provide 7.0 g. (23%) of 4'-nitrobenzyl 7-phenoxyacetamido-3-methylenecepham-4-carboxylate-1-oxide.

EXAMPLE 32

4'-Nitrobenzyl 3-methyl-2-(2-aminosulfinyl-4-oxo-3-phenoxyacetamido-1-azetidinyl)-3-butenoate To a solution of 5 g. of 4'-nitrobenzyl 3-methyl-2-(2-chlorosulfinyl-4-oxo-3-phenoxyacetamido-1-azetidinyl)-3-butenoate in toluene was added a solution of 5 g. of sodium cyanate in 100 ml. of water. After 1 hour at room temperature, the organic phase was separated, dried (MgSO₄) and evaporated in vacuo to dryness to provide a mixture of the title product and 4'-nitrobenzyl 6-phenoxyacetamidopenicillanate sulfoxide. For the title product: nmr (CDCl₃) δ1.96 (s, 3), 4.55

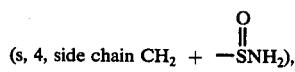
(s, 4, side chain CH₂ + —SNH₂), 4.88 (d, 1, J=4.5 Hz, β-lactam H), 5.0–5.5 (m, 5), 5.72 (dd, 1, J=4.5 and 9.0 Hz, β-lactam H), 7.74 (d, 1, J=9.0 Hz, —NH) and 6.9–8.4 (m, 9, ArH).

Anal. Calcd. for C₂₃H₂₄N₄O₈S: C, 53.48; H, 4.68; N, 10.85; O, 24.78; S, 6.21.

Found: C, 53.69; H, 4.77; N, 10.62; S, 5.90.

EXAMPLE 33

2',2',2'-Trichloroethyl 3-methyl-2-[2-chlorosulfinyl-4-oxo-3-(2-tert-butoxycarbonylamino-2-phenylacetamido)-1-azetidinyl]-3-butenoate A solution of 2.85 g. (5 mmol.) of 2',2',2'-trichloroethyl 6-(2-tert-butoxycarbonylamino-2-phenylacetamido)-2,2-dimethylpenam-3-carboxylate 1-oxide in 175 ml. of toluene was dried azeotropically by distillation of about 50 ml. of toluene from the mixture. To the dried solution were added 0.685 g. (5.5 mmol.) of N-chlorosuccinimide. The resulting mixture was refluxed for 70 minutes. After the mixture was allowed to cool to room temperature, it was filtered and evaporated in vacuo to dryness to provide the title product (contaminated with succinimide): nmr (CDCl₃) δ1.40 (s, 9, tert-butyl), 1.95 (s, 3, CH(CH₃):CH₂), 4.82 (bs, 2, ester CH₂), 5.20 (m, 3, CH(CH₃):CH₂ + CHCOOCH₂CCl₃), 5.38 (d, 1, J=4.5 Hz, azetidinone C₂—H), 5.80 (m, 1, azetidinone C₃—H) and 7.34 (s, 5, ArH).

EXAMPLE 34

2',2',2'-Trichloroethyl 3-methyl-2-[2-sulfino-4-oxo-3-(2-tert-butoxycarbonylamino-2-phenylacetamido)-1-azetidinyl]-3-butenoate The product sulfinyl chloride from Example 33 was dissolved in 50 ml. of acetone and 100 ml. of 1N.HCl. The resulting solution was stirred at ice bath temperature for two hours. The mixture was then extracted with ethyl acetate. The organic extracts were combined, washed with brine, and then extracted with aqueous sodium bicarbonate. The aqueous extracts were then combined and layered with ethyl acetate. The pH of the aqueous layer was then adjusted to about 2 with 1N.HCl. The ethyl acetate layer was then separated, washed with brine, dried over anhydrous MgSO$_4$ and evaporated in vacuo to dryness to provide 1.032 g. of the title product: nmr (CDCl$_3$) δ1.44 (s, 9, tert-butyl), 1.94 (s, 3, CHC(CH$_3$):CH$_2$), 4.82 (s, 2, —CH$_2$CCl$_3$), 5.22 (m, 4, CHCOOCH$_2$CCl$_3$ + CHC(CH$_3$):CH$_2$ + azetidinone C$_2$—H), 5.74 (dd, 1, J=4.5 and 9.0 Hz, azetidinone C$_3$—H), 7.34 (s, 5, ArH), 8.10 (bs, 1, —NH), and 9.0 (bs, 1,—SOOH).

EXAMPLE 35

2',2',2'-Trichloroethyl 3-methyl-2-[2-chlorosulfinyl-4-oxo-3-(2-thienylacetamido)-1-azetidinyl]-3-butenoate A. A solution of 3.5 g. of 2',2',2'-trichloroethyl 6-(2-thienylacetamido)-2,2-dimethylpenam-3-carboxylate 1-oxide in 350 ml. of toluene was prepared and dried azeotropically by distilling 100 ml. of toluene from the mixture. After cooling, 1 g. of N-chlorosuccinimide was added. The reaction mixture was refluxed for 50 minutes, cooled, and filtered. A 5 ml. portion was evaporated in vacuo to dryness to provide the title product: nmr (CDCl$_3$) δ1.87 (s, 3, CH(CH$_3$):CH$_2$), 3.82 (s, 2, side chain CH$_2$), 4.80 (ABq, 2, J=13 Hz, —CH$_2$CCl$_3$), 5.18 (m, 3, —CH(CH$_3$):CH$_2$), 5.50 (d, 1, J=4.5 Hz, azetidinone C$_2$—H) and 6.05 (m, 1, azetidinone C$_3$—H).

B. Cyclization to exomethylenecepham.

To the remainder of the toluene solution of the sulfinyl chloride product from part (A) was added 1.5 ml. of anhydrous stannic chloride. The mixture was allowed to stir for 1 hour. (Ethyl acetate (250 ml.) was added, and the resulting solution was washed with three 400 ml.-portions of brine, dried over anhydrous MgSO$_4$, and evaporated in vacuo to dryness. The product thereby obtained was dissolved in 30 ml. of ethyl acetate; 350 mg. of 2',2',2'-trichloroethyl 7-(2-thienylacetamido)-3-methylenecepham-4-carboxylate 1-oxide crystallized and was separated: nmr (DMSO$_d$-6) δ3.38 (bs, 2, C$_2$—H), 3.80 (s, 2, side chain CH$_2$), 5.02 (s, 2, —CH$_2$CCl$_3$), 5.04 (d, 1, J=4 Hz, C$_6$—H), 5.4–5.8 (m, 4), 6.8–7.4 (m, 3, thienyl), and 8.16 (d, 1, J=8 Hz, —NH).

I claim:

1. The process for preparing a 3-methylenecepham sulfoxide of the formula

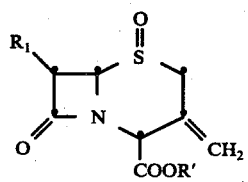

by reacting a compound of the formula

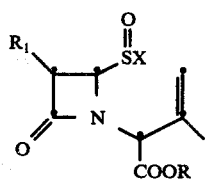

with a Lewis acid type Friedel-Crafts catalyst, a Bronsted proton acid type Friedel-Crafts catalyst or a metathetic cation-forming agent in a dry inert organic solvent, or dissolving such compound in a Bronsted acid selected from the group consisting of methanesulfonic acid, trifluoromethanesulfonic acid, trilfuoroacetic acid, trichloroacetic acid, or dichloroacetic acid; wherein in the above formulae R is a carboxylic acid protecting group;
R' is R or hydrogen;
R$_1$ is (1) an imido group of the formula

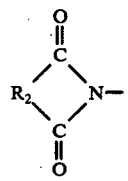

wherein R$_2$ is C$_2$-C$_4$ alkenylene, C$_2$-C$_4$ alkylene, 1,2-phenylene, 1,2-cyclohexenylene; or 2. an amido group of the formula

wherein R$_3$ is a. hydrogen, C$_1$-C$_3$ alkyl, halomethyl, cyanomethyl or 3-(2-chlorophenyl)-5-methylisoxazol-4-yl;

b. benzyloxy, 4-nitrobenzyloxy, 2,2,2-trichloroethoxy, tert-butoxy, or 4-methoxybenzyloxy;

c. the group R" wherein R" is phenyl or phenyl substituted with 1 or 2 substituents independently selected from the group consisting of halo, protected hydroxy, nitro, cyano, trifluoromethyl, C$_1$-C$_3$ alkyl, and C$_1$-C$_4$ alkoxy;

d. an arylalkyl group of the formula

wherein R$^o$ is R" as defined above, 2-thienyl, 3-thienyl or 1,4-cyclohexadienyl, m is 0 or 1, and Q is O or S subject to the limitation that when m is 1, R$^o$ is R";

e. a substituted arylalkyl group of the formula

wherein R$^o$ is as defined above and W is protected hydroxy or protected amino;

3. an imido group of the formula

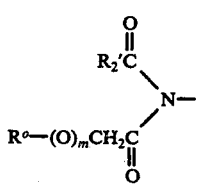

wherein R$^o$ and m are as defined hereinabove and R$_2$' is C$_1$-C$_3$ alkyl, C$_1$-C$_6$ haloalkyl, C$_1$-C$_3$ alkoxy or trichloroethoxy; or R$_1$ is 4. an imidazolidinyl group of the formula

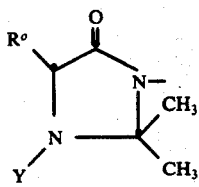

wherein R° is as defined above and Y is acetyl or nitroso; and X is
1. chloro or bromo;
2. a group of the formula —OR$_4$ wherein R$_4$ is hydrogen, C$_1$-C$_{10}$ alkyl, aryl (C$_1$-C$_3$ alkyl) or C$_1$-C$_6$ haloalkyl;
3. a group of the formula -SR$_5$ wherein R$_5$ is C$_1$-C$_6$ alkyl, aryl or aryl (C$_1$-C$_3$ alkyl); or
4. a group of the formula

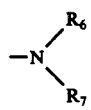

wherein
a. R$_6$ is hydrogen and R$_7$ is hydrogen, R" is as defined hereinabove, or a group of the formula —NHR$_8$ wherein R$_8$ is aminocarbonyl, C$_1$-C$_3$ alkylaminocarbonyl, C$_1$-C$_3$ alkylcarbonyl, C$_1$-C$_3$ alkoxycarbonyl or tosyl;
b. R$_6$ is —COOR$_9$ or —COR$_9$ and R$_7$ is —NHCOOR$_9$ or —NHCOR$_9$ wherein R$_9$ is C$_1$-C$_6$ alkyl or phenyl; or wherein
c. R$_6$, R$_7$ and the nitrogen atom to which they are bonded taken together form an imido group of the formula

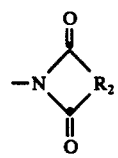

wherein R$_2$ is as defined hereinabove; and when R6 is —COOR$_9$ or —COR$_9$ and R$_7$ is —NHCOOR$_9$ or —NHCOR$_9$, R$_3$ is additionally a heteroarylmethyl group of the formula R""CH$_2$— wherein R"" is 2-furyl, 3-furyl, 2-thiazolyl or 5-isoxazolyl; with the limitations that when X is bromo, R$_1$ is only an imido group of the formula

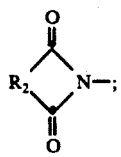

when the cyclizing agent is a metathetic caton-forming agent or a Lewis acid, X is only chloro or bromo; and when R is an acid labile carboxylic acid protecting group, the product is a 3-methylenecepham-4-carboxylic acid sulfoxide.

2. The process of claim 1 wherein R is methyl, tert-butyl, benzyl, 4-methoxybenzyl, C$_2$-C$_4$ alkanoyloxymethyl, 2-iodoethyl, 4-nitrobenzyl, diphenylmethyl (benzhydryl), phenacyl, 4-halophenacyl, dimethylallyl, 2,2,2-trichloroethyl, tri(C$_1$-C$_3$alkyl)silyl or succinimidomethyl.

3. The process of claim 2 wherein R is methyl, 2-iodoethyl, 4-nitrobenzyl, 4-halophenacyl and 2,2,2-trichloroethyl.

4. The process of claim 1 wherein a metal halide Lewis acid type catalyst or a metathetic cation-forming agent is employed.

5. The process of claim 4 wherein a metathetic cation-forming agent is employed.

6. The process of claim 5 wherein the metathetic cation-forming agent is an anhydrous silver salt.

7. The process of claim 6 wherein silver p-toluenesulfonate is employed.

8. The process of claim 7 wherein the reaction temperature is about 20° to about 80° C.

9. The process of claim 4 wherein a metal halide Lewis acid type catalyst is employed.

10. The process of claim 9 wherein the catalyst is aluminum chloride, stannic chloride, stannic bromide, zinc chloride, zinc bromide, antimony pentachloride, titanium tetrachloride, ferric chloride, gallium trichloride, zirconium tetrachloride, mercuric chloride or chromium trichloride.

11. The process of claim 9 wherein the inert organic solvent is an aromatic hydrocarbon solvent or a halogenated aliphatic hydrocarbon solvent.

12. The process of claim 9 wherein the catalyst is stannic chloride, zinc chloride, zinc bromide, zirconium tetrachloride or titanium tetrachloride.

13. The process of claim 9 wherein the reaction is effected with about 1:1 equivalents of the Friedel-Crafts catalyst in an aromatic hydrocarbon solvent or a halogenated aliphatic hydrocarbon solvent at a temperature of about 10° to about 115° C.

14. The process of claim 13 wherein stannic bromide, stannic chloride or antimony pentachloride is employed at a temperature of about 10° to about 40° C.

15. The process of claim 14 wherein the reaction is effected at room temperature with stannic chloride.

16. The process of claim 13 wherein the reaction is effected with aluminum chloride, zinc chloride, zinc bromide, ferric chloride, gallium trichloride, zirconium tetrachloride, mercuric chloride or chromium trichloride at a temperature of about 40° to about 115° C.

17. The process of claim 13 wherein titanium tetrachloride is employed at a temperature of about 40° to about 100° C.

18. The process of claim 13 wherein X is chloro, R$_1$ is an amido group of the formula

and R$_3$ is an arylalkyl group of the formula R°—(O)-$_m$—CH$_2$—.

19. The process of claim 18 wherein the Friedel-Crafts catalyst is stannic chloride.

20. The process of claim 19 wherein R$_3$ is benzyl, 2-thienylmethyl, or phenoxymethyl.

21. The process of claim 1 wherein a Bronsted proton acid type catalyst is employed.

22. The process of claim 21 wherein X is chloro or bromo.

23. The process of claim 21 wherein X is a group of the formula —OR$_4$, a group of the formula —SR$_5$ or a group of the formula

24. The process of claim 21 wherein the reaction is effected in an aromatic hydrocarbon solvent or a halogenated aliphatic hydrocarbon solvent at a temperature of about 70° to about 115° C.

25. The process of claim 24 wherein the Friedel-Crafts catalyst is a conjugate Friedel-Crafts acid catalyst of the type $HMA_{4,6}$.

26. The process of claim 25 wherein the Friedel-Crafts catalyst is $HBF_4$, $HAlCl_4$, $HAsF_6$ or $HAlBr_4$.

27. The process of claim 24 wherein the Friedel-Crafts catalyst is an acidic chalcide.

28. The process of claim 27 wherein the catalyst is phosphorous pentoxide.

29. The process of claim 24 wherein the Bronsted proton acid catalyst is methanesulfonic acid, ethanesulfonic acid, trifluoroacetic acid, trichloroacetic acid, dichloroacetic acid, sulfuric acid, phosphoric acid, polyphosphoric acid, perchloric acid, chlorosulfonic acid, or fluorosulfonic acid.

30. The process of claim 29 wherein the Bronsted proton acid catalyst is methanesulfonic acid, trifluoroacetic acid, phosphoric acid, sulfuric acid or polyphosphoric acid.

31. The process of claim 21 wherein the starting material is dissolved in methanesulfonic acid, ethanesulfonic acid, trifluoroacetic acid, trichloroacetic acid or dichloroacetic acid at room temperature and maintained in solution for about 10 to about 30 minutes.

32. The process of claim 31 wherein X is a group of the formula $-OR_4$, a group of the formula $-SR_5$ or a group of the formula

33. The process of claim 32 wherein $R_1$ is an amido group of the formula

and $R_3$ is an arylalkyl group of the formula $R^o-(O)_m-CH_2-$.

34. The process of claim 33 wherein methanesulfonic acid is employed as the cyclizing agent.

35. The process of claim 1 wherein R is benzhydryl, 4-methoxybenzyl, tert-butyl, or tri($C_1-C_3$ alkyl)silyl and R' is hydrogen.

* * * * *